US011327136B2

(12) United States Patent
Keupp et al.

(10) Patent No.: US 11,327,136 B2
(45) Date of Patent: May 10, 2022

(54) SINGLE-POINT DIXON METHOD FOR FAT-WATER SEPARATION IN CHEMICAL EXCHANGE SATURATION TRANSFER MAGNETIC RESONANCE IMAGING

(71) Applicant: KONINKLIJKE PHILIPS N.V., Eindhoven (NL)

(72) Inventors: Jochen Keupp, Rosengarten (DE); Holger Eggers, Ellerhoop (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/960,906

(22) PCT Filed: Jan. 7, 2019

(86) PCT No.: PCT/EP2019/050189
§ 371 (c)(1),
(2) Date: Jul. 9, 2020

(87) PCT Pub. No.: WO2019/137858
PCT Pub. Date: Jul. 18, 2019

(65) Prior Publication Data
US 2020/0348382 A1 Nov. 5, 2020

(30) Foreign Application Priority Data

Jan. 12, 2018 (EP) .................................. 18151467

(51) Int. Cl.
*G01R 33/56* (2006.01)
*G01R 33/24* (2006.01)
(Continued)

(52) U.S. Cl.
CPC ....... *G01R 33/5605* (2013.01); *G01R 33/243* (2013.01); *G01R 33/4828* (2013.01); *G01R 33/583* (2013.01)

(58) Field of Classification Search
CPC ............. G01R 33/5605; G01R 33/243; G01R 33/4828; G01R 33/583; A61B 5/055
See application file for complete search history.

(56) References Cited

U.S. PATENT DOCUMENTS 8,536,866 B2 * 9/2013 Van Zijl ............... G01R 33/483
324/309
8,588,890 B2  11/2013 Kimura
(Continued)

OTHER PUBLICATIONS

Zhou J, Payen JF, Wilson DA, Traystman RJ, van Zijl PCM. Using the amide proton signals of intracellular proteins and peptides to detect pH effects in MRI. Nature Medicine 2003; 9:1085-1090.
(Continued)

*Primary Examiner* — Susan S Lee

(57) ABSTRACT

The invention provides for a medical imaging system (100, 300). The medical imaging system comprises a processor (104). Execution of machine executable instructions (120) causes the processor to: receive (200) magnetic resonance imaging data (122) comprising a Z-spectrum acquisition (124) for a set of saturation frequency offsets (126) and at least one reference saturation frequency offset (128); reconstruct (202) saturation frequency offset complex image data (130); reconstruct (204) a B0 map (132), a water image (134), and a fat image (136) according to a Dixon-type magnetic resonance imaging protocol; calculate (206) a water phase angle (138) using the water image and/or the fat image; calculate (208) rotated complex image data (140) by rotating the phase of the saturation frequency offset complex image data such that the complex water signal is aligned with a real axis for each voxel; perform (210) a B0 correction by calculating shifted complex image data (142); calculate (212) a frequency dependent phase angle (144) descriptive of a phase angle between the complex water signal and the complex fat signal for each of the set of
(Continued)

saturation frequency offsets using a fat signal model comprising at least two fat species; calculate (214) a residual fat component correction factor (150) by projecting the complex fat signal onto the real axis for each of the set of saturation frequency offsets; and calculate (216) corrected water Z-spectrum image data (152) by subtracting the residual fat component correction factor for each of the set of saturation frequency offsets from the real component of the shifted complex image data.

14 Claims, 12 Drawing Sheets

(51) Int. Cl.
*G01R 33/48* (2006.01)
*G01R 33/58* (2006.01)

(56) References Cited

U.S. PATENT DOCUMENTS

| | | | | |
|---|---|---|---|---|
| 8,686,727 | B2* | 4/2014 | Reddy | G01R 33/5601 |
| | | | | 324/307 |
| 9,519,040 | B2 | 12/2016 | Ma et al. | |
| 9,709,511 | B2* | 7/2017 | Lee | G16C 20/70 |
| 2015/0051474 | A1* | 2/2015 | Eggers | G01R 33/5605 |
| | | | | 600/410 |
| 2016/0334485 | A1* | 11/2016 | Miyoshi | G01R 33/5605 |
| 2021/0063519 | A1* | 3/2021 | Keupp | G01R 33/5605 |

OTHER PUBLICATIONS

Jones CK, Schlosser MJ, Zijl PCM, Pomper MG, Golay X, Zhou J. Amide proton transfer imaging of human brain tumors at 3T. Magn Reson Med 2006; 56:585-592.

Zhou J, Tryggestad E, Wen Z, Lal B, Zhou T, Grossman R, Wang S, Yan K, Fu DX, Ford E, Tyler B, Blakeley J, Laterra J, van Zijl PCM. "Differentiation between glioma and radiation necrosis using molecular magnetic resonance imaging of endogenous proteins and peptides" Nature Medicine 2011; 17:130.

Ma J. "A single-point Dixon technique for fat-suppressed fast 3D gradient-echo imaging with a flexible echo time" J Magn Reson Imaging 2008; 27:881-890.

Dixon WT. "Simple proton spectroscopic imaging" Radiology 1984; 153:189.

Search Report and Written Opinion from PCT/EP2019/050189 dated Apr. 3, 2019.

Reeder SB, Wen Z, Yu H, Pineda AR, Gold GE, Markl M, Pelc NJ Multicoil Dixon chemical species separation with an iterative least-squares estimation method. Magn Reson Med 2004; 51:35.

Kim M, Gillen J, Landman BA, Zhou J, van Zijl PC. Water saturation shift referencing (WASSR) for chemical exchange saturation transfer (CEST) experiments. Magn Reson Med 2009; 61:1441.

Moritz Zaiss and Peter Bachert "Chemical Exchange Saturation Transfer and MR Z Spectroscopy in Vivo . . . " 2013 Phys. Med. Biol. 58 R221.

Van Vijl et al "Proton Chemical Exchange Saturation Transfer MRS and MRI" E Mag Res. vol. 5, 2016.

Tamar Hoory et al: "Effect of Gd-DTPA induCED susceptibility on single-point dixon fat/water separation", Magnetic Resonance in Medicine., vol. 59, No. 4, Feb. 26, 2008 (Feb. 26, 2008), pp. 925-929.

Yu H et al: "Singe acquisition water-fat separation: Feasibility study for dynamic imaging", Magnetic Resonance in Medicine, John Wiley & Sons, Inc, US, vol. 55, Jan. 1, 2006 (Jan. 1, 2006),pp. 413-422.

Jingfei Ma: "Dixon techniques for water and fat imaging", Journal of Magnetic Resonance Imaging, Society for Magnetic Resonance Imaging, Oak Brook, IL, US, vol. 28, No. 3,Sep. 1, 2008 (Sep. 1, 2008), pp. 543-558.

Jochen Keupp et al.: "Intrinsic Field Homogeneity Correction in Fast Spin Echo based Amide Proton Transfer MRI", Proceedings of the International Society for Magnetic Resonance in Medicine, ISMRM, 20TH Annual Meeting and Exhibition, Melbourne, Australia, May 5-11, 2012, Apr. 21, 2012.

* cited by examiner

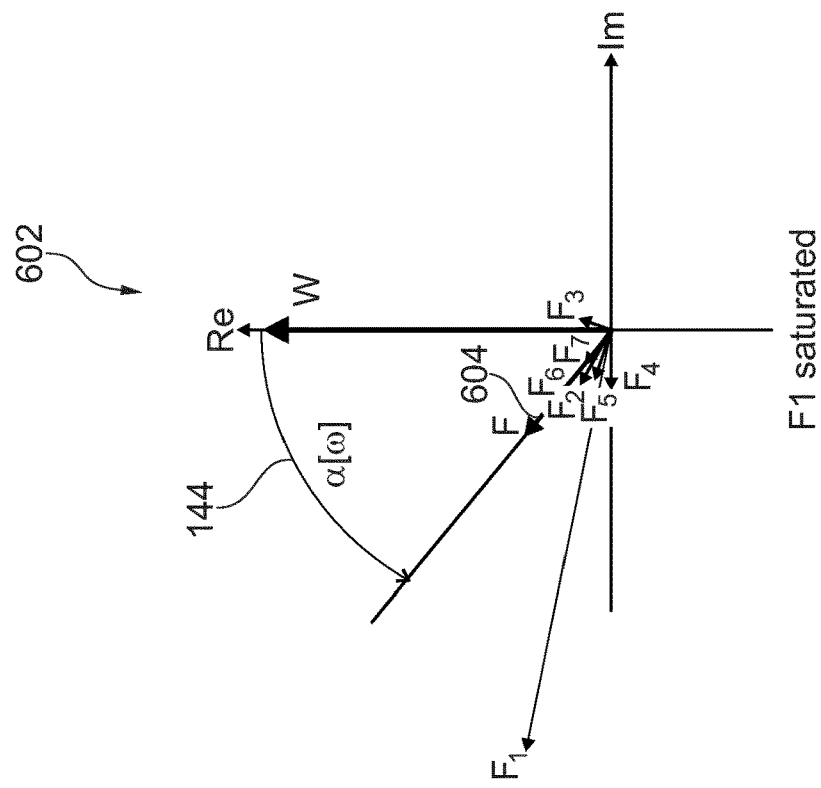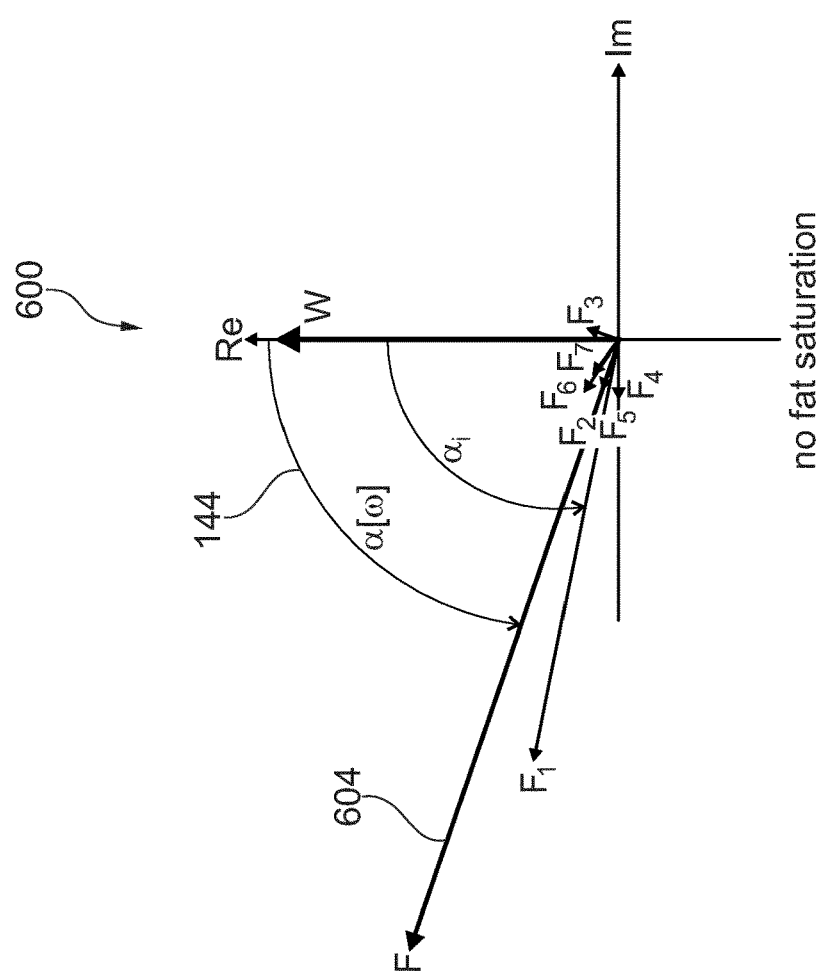
Fig. 6

SINGLE-POINT DIXON METHOD FOR FAT-WATER SEPARATION IN CHEMICAL EXCHANGE SATURATION TRANSFER MAGNETIC RESONANCE IMAGING

CROSS REFERENCE TO RELATED APPLICATIONS

This application is a U.S. national phase application of International Application No. PCT/EP2019/050189 filed on Jan. 7, 2019, which claims the benefit of EP Application Serial No. 18151467.0 filed on Jan. 12, 2018 and is incorporated herein by reference.

TECHNICAL FIELD

The invention relates to magnetic resonance imaging, in particular it relates to CEST or APT magnetic resonance imaging.

BACKGROUND OF THE INVENTION

Magnetic resonance imaging (MRI) scanners rely on a large static magnetic field ($B_0$) to align the nuclear spins of atoms as part of the procedure for producing images within the body of a patient. These images can reflect various quantities or properties of the subject. For example, the density of hydrogen protons can be measured and resolved spatially. However, often times a compound or metabolite is so dilute that as a practical matter it is not possible to image it directly.

Therefore, techniques such as chemical exchange saturation transfer (CEST) MRI have been developed. In CEST imaging, the presence of dilute metabolites with exchangeable protons is measured. The protons of the metabolites which can be studied using CEST are able to exchange positions with the protons from water. A saturation pulse can be used to suppress the MRI signal from the exchangeable protons of the metabolites. Because the protons are exchangeable, they trade places with the water protons. Because the protons from the metabolites were targeted with a saturation pulse they do not contribute to the measured MRI signal for a period of time. This is true even when the protons from the metabolites were exchanged with the water protons. This then has the effect of reducing the measured MRI signal from the water protons. By performing saturation pulses at different frequency offsets and measuring the effect on the measured MRI signal information about the presence of dilute metabolites or other substances can be determined. There are a variety of techniques that are related to the CEST technique. One example is amide proton transfer (APT) MRI.

The journal article Zaiss et al. "Chemical exchange saturation transfer (CEST) and MR Z-spectroscopy in vivo: a review of theoretical approaches and methods," Phys. Med. Biol. 58 (2013) R221-R269, provides a topical review of CEST and Z-spectroscopy.

SUMMARY OF THE INVENTION

In one aspect the invention provides for a medical imaging system, a computer program product, and a method in the independent claims. Embodiments are given in the dependent claims.

When performing CEST, measurements are typically made at saturation frequency offsets symmetrically around the resonance frequency of water. This is done because the saturation pulses may also have an effect on the water signal. By making measurements symmetrically above and below the water resonance, the two can be compared and one measurement can be used as a baseline. The presence of fat can disrupt this. Moreover, normal fat suppression techniques can also affect these measurements.

Embodiments of the invention may provide for improved CEST imaging in the presence of fat by using a fat signal model with at least two fat species to correct for the presence of fat.

In one aspect, the invention provides for a medical imaging system. The medical imaging system comprises a memory for storing machine-executable instructions. The medical imaging system further comprises a processor for controlling the medical imaging system. The medical imaging system may take different forms in different examples. In some examples the medical imaging system is a system for processing or modifying images or data related to images. In other examples the medical imaging system may also comprise components for acquiring medical imaging data which is then processed or may be processed into data suitable for rendering.

Execution of the machine-executable instructions causes the processor to receive MRI data. The MRI data comprises a Z-spectrum acquisition for a set of saturation frequency offsets and at least one reference saturation frequency offset. A Z-spectrum as used herein encompasses data or data which may be plotted that displays the free water signal plotted against the frequency offset for the saturation pulse. This technique is often referred to as Z-spectroscopy. The Z-spectrum acquisition is according to or suitable for a CEST MRI protocol. The Z-spectrum acquisition for the at least one reference saturation frequency offset comprises data from multiple echo shifts or echo times. The Z-spectrum acquisition for each of the set of frequency offsets and the at least one reference saturation frequency offset is descriptive of complex image data comprising a complex water signal and a complex fat signal.

Execution of the machine-executable instructions further causes the processor to reconstruct saturation frequency offset complex image data for each of the set of saturation frequency offsets. The frequency offset complex image data comprises voxels. All of the different saturation frequency offset complex image data may for example have the same or equivalent voxels.

Execution of the machine-executable instructions further causes the processor to reconstruct a B0 map, a water image, and/or a fat image using the data from multiple echo shifts or echo times according to a Dixon MRI protocol. Execution of the machine-executable instructions further causes the processor to calculate a water phase angle using the water image and/or the fat image. Execution of the machine-executable instructions further cause the processor to calculate rotated complex image data by rotating the phase of the saturation frequency offset complex image data for each of the voxels using the water phase angle such that the complex water signal is aligned with a real axis for each voxel. This causes the water signal to be described by a purely real number for each voxel.

Execution of the machine-executable instructions further causes the processor to perform a B0 correction by calculating shifted complex image data using the rotated complex image data for each of the set of saturation frequency offsets and for each of the voxels using the B0 map.

Execution of the machine-executable instructions further causes the processor to calculate a frequency dependent phase angle descriptive of the phase angle between the complex water signal and the complex fat signal for each of the set of saturation frequency offsets using a fat signal model comprising at least two fat species. This step may be beneficial because the fat has multiple resonances. By using a fat signal model that has more than one resonance the value of the frequency dependent phase angle may be more accurate.

Execution of the machine-executable instructions further causes the processor to calculate a residual fat component correction factor by projecting the complex fat signal onto the real axis for each of the set of saturation frequency offsets and for each of the voxels using the frequency dependent phase angle. Knowledge of the frequency dependent phase angle enables the projection of the complex fat signal onto the real axis. Execution of the machine-executable instructions further causes the processor to calculate corrected water Z-spectrum image data by subtracting the correction factor for each of the set of saturation frequency offsets and for each of the voxels from the real component of the shifted complex image data.

This embodiment may be beneficial because it may provide for more accurate measurement of the water Z-spectrum image data. Because the Z-spectrum acquisition comprises both a water signal and a fat signal there has been no suppression of the fat signal. This means that any suppression of the fat signal will not interfere with the proper calculation of the water Z-spectrum image data. The water Z-spectrum image data as used herein is data which may be in the form of or may be suitable for generating a Z-spectrum or z-spectrum image.

In another embodiment, the two fat peaks of the fat signal model are for example those from the hydrogen atoms in $CH_2$ and $CH_3$.

The B0 correction for example can be performed by interpolating the Z-spectrum data. This may for example be accomplished by shifting the entire Z-spectrum along the direction of the saturation frequency offsets.

In another embodiment, the medical imaging system further comprises a MRI system configured for acquiring the MR data from a subject within an imaging zone. The memory further stores pulse sequence commands. The pulse sequence commands are configured to acquire the MR data according to a CEST MRI protocol. Execution of the machine-executable instructions further causes the processor to control the MRI system with the pulse sequence commands to acquire the MRI data.

In another embodiment, the pulse sequence commands are configured to acquire the Z-spectrum acquisition for the set of saturation frequency offsets and the at least one reference saturation frequency offsets with the water signal and the fat signal by using either the same echo shift or the same echo time. The pulse sequence commands are further configured to acquire the Z-spectrum acquisition for the remaining of the at least one reference saturation frequency offset using at least one further echo shift or at least one further echo time. The use of the further echo shift or the further echo time enables the Dixon type MRI protocol to be performed in order to determine the B0 map, the water image, and/or the fat image.

In another embodiment, the pulse sequence commands are according to any one of the following: a spin echo protocol, a fast or turbo spin echo protocol, an echo planar imaging protocol, a gradient echo imaging protocol, and a steady-state free procession imaging protocol.

In another embodiment, the pulse sequence commands are configured to acquire the MR data without fat suppression pulse sequence commands. This embodiment may be beneficial because the fat suppression pulse sequence commands may cause distortions or errors in a Z-spectrum image. The presence of both water signal and fat signal in the MR data implies that there has been no fat suppression pulse sequence commands.

In another embodiment, the pulse sequence commands are configured for using a specific echo shift or a specific echo time such that the water signal and the fat signal are neither in-phase nor out of phase when the frequency saturation offsets and the at least one reference frequency saturation frequency offset use the same echo shift or the same echo time. In this embodiment, the pulse sequence commands are configured for using a specific echo shift or specific echo time such that the phase between the water and fat signals is unequal to 0 degree and unequal to 180 degrees when the set of saturation frequency offsets and the at least one reference saturation frequency offset use the same echo shift or the same echo time.

The pulse sequence commands may be configured using a specific echo shift or a specific echo time. This may be done such that the phase between the water and the fat signals is different from 0° and also different from 180° by at least a predefined minimum range of angles. For example this may be plus or minus 5°.

In another embodiment, the memory further comprises fat calibration pulse sequence commands. The fat calibration pulse sequence commands are configured for measuring the line width and/or one or more relaxation rates of the two or more fat species. Execution of the machine-executable instructions further causes the processor to acquire fat calibration MR data by controlling the MRI system with the fat calibration pulse sequence commands and also to calibrate the fat signal model for the saturation frequency offsets using the MR data. The fat calibration MR data may in one example be spectroscopy data. In another example image data may be processed to calibrate the fat signal model.

In another embodiment, execution of the machine-executable instructions further causes the processor to identify voxels which contain more than a predetermined fraction of fat. The fat image could for example be used for this. Execution of the machine-executable instructions further causes the processor to use the fat calibration MR data from the chosen voxels for calibrating the fat signal model. For example, the acquisition of fat calibration MR data could be acquired from a region containing only the chosen voxels or a predetermined number of chosen voxels. In other examples the fat calibration MR data is reconstructed into images or converted to image space and image data from the chosen voxels is then used for the calibration of the fat signal model.

The fat calibration pulse sequence commands may also localize the fat in different locations within a subject's body so that there can be a local or spatially dependent calibration of the fat signal model.

This embodiment may be equivalent to a preparatory experiment or preparatory measurements which are used to refine the resonance frequency offsets, the resonance areas, and in particular the line widths or relaxation rates of individual fat species possibly at different locations. This may be done in a way that is dependent upon the saturation frequency offset within the set of saturation frequency offsets and also the at least one reference saturation frequency offset. This may for example be accomplished by means of spectroscopy or by relying on the identification of pure fat signals within a region of interest or locations within a region of interest.

In another embodiment, the phase between the water signal and the fat signal are within any one of the following ranges when the set of saturation frequency offsets and the at least one reference saturation frequency offset use the same echo shift or the same time shift: between 5° and 175°, and between 185° and 355°. In this example the water signal and the fat signal are neither in-phase nor out-of-phase.

In another embodiment, the Dixon MRI protocol is a multi-point Dixon MRI protocol configured for using at least two different echo shifts or two different echo times for reconstructing the B0 map with the water image and/or the fat image. The at least two different echo shifts may include the same echo shift used for all of the Z-spectrum acquisition for the set of saturation frequency offsets. The at least two different echo times may include the same echo time used for all of the Z-spectrum acquisition for the set of frequency offsets.

In another embodiment, the at least one reference saturation frequency offset is performed at a frequency offset S0.

In another embodiment, S0 is any one of the following: a largely detuned frequency offset, less than −1000 ppm, or −1560 ppm, or the acquisition is performed without any saturation pulse. This embodiment may be beneficial because it may provide for an accurate measurement of the B0 field, the water image and the fat image using the Dixon MRI protocol.

In another embodiment, execution of the machine-executable instructions further causes the processor to calculate a fat corrected CEST MR image using the corrected water Z-spectrum image data for each of the set of saturation frequency offsets. This embodiment may be beneficial because the Z-spectrum was constructed without the use of fat suppression. It may be more accurate in this case.

In another embodiment, execution of the machine-executable instructions further causes the processor to calculate a fat corrected CEST MR image using the corrected water Z-spectrum image data for each of the set of saturation frequency offsets by calculating the magnetization transfer asymmetry. This embodiment may be beneficial because the use of fat saturation pulses may cause errors particularly when using the magnetization transfer asymmetry. The fat corrected CEST MR image may therefore be more accurate.

In another embodiment, execution of the machine-executable instructions further causes the processor to calculate a fat corrected CEST MR image by fitting a symmetric model function to the corrected water Z-spectrum image data for each of the set of saturation frequency offsets. The fat corrected CEST MR image is further calculated by calculating a CEST MRI data by using a difference between the real component of the corrected water Z-spectrum image data to the symmetric model function at respective saturation frequency offsets. The fat corrected CEST MR image is further calculated by normalizing the CEST MRI data to S0. The calculation of the fat corrected CEST MR image is then further performed by calculating a CEST MR image using the normalized CEST MRI data.

This may provide for an improved means of calculating a fat corrected CEST MR image. For example the symmetric model function may in one example be a Lorentz-Gauss function.

In another embodiment, the CEST MRI protocol is an APT weighted MRI protocol. This embodiment may be beneficial because the APT weighted MRI protocols are particularly susceptible to errors caused by the presence of fat.

In another aspect, the invention provides for a method of medical image processing or for operating a medical imaging system. The method comprises receiving MRI data. The MRI data comprises a Z-spectrum acquisition for a set of saturation frequency offsets and at least one reference saturation frequency offset. The Z-spectrum acquisition is according to a CEST MRI protocol. The Z-spectrum acquisition for the least one reference saturation frequency offset comprises data from multiple echo shifts or for multiple echo times. The Z-spectrum acquisition for each of the set of frequency offsets and the at least one reference saturation frequency offset is descriptive of complex image data comprising a complex water signal and a complex fat signal. The method further comprises reconstructing saturation frequency offset complex image data for each of the set of saturation frequency offsets from the Z-spectrum acquisition. The saturation frequency offset complex image data comprises voxels.

The method further comprises reconstructing the B0 map, a water image, and a fat image using the data from multiple echo shifts or multiple echo times according to a Dixon-type MRI protocol. The method further comprises calculating a water phase angle using the water image and/or the fat image. The method further comprises calculating a rotated complex image data by rotating the phase of the saturation frequency offset complex image data for each of the voxels using the water phase angle such that the complex water signal is aligned with the real axis of the complex plane for each voxel.

The method further comprises performing a B0 correction by calculating shifted complex image data using the rotated complex image data for each of the set of saturation frequency offsets and for each of the voxels using the B0 map. The B0 map introduces a shift which is then used voxel-by-voxel to calculate the shifted complex image data. The method further comprises calculating a frequency dependent phase angle descriptive of the phase angle between the water signal and the fat signal for each of the set of saturation frequency offsets using a fat signal model comprising at least two fat specifies. The method further comprises calculating a residual fat component correction factor by projecting the complex fat signal onto the real axis for each of the set of saturation frequency offsets and for each of the voxels using the frequency dependent phase angle. The method further comprises calculating corrected water Z-spectrum image data by subtracting the correction factor for each of the set of saturation frequency offsets and for each of the voxels from the real component of the shifted complex image data.

In another aspect, the invention comprises a computer program product comprising machine-executable instructions for execution by a processor controlling a medical imaging system. Execution of the machine-executable instructions causes the processor to receive MRI data. The MRI data comprises a Z-spectrum acquisition for a set of saturation frequency offsets and at least one reference saturation frequency offset. The Z-spectrum acquisition is according to a CEST MRI protocol. The Z-spectrum acquisition of the at least one reference saturation frequency offset comprises data for multiple echo shifts or echo times. The Z-spectrum acquisition for each of the set of frequency offsets and the at least one reference saturation frequency offset is descriptive of a complex image data comprising a complex water signal and a complex fat signal.

Execution of the machine-executable instructions further causes the processor to reconstruct saturation frequency offset complex image data for each of the set of saturation frequency offsets using the Z-spectrum acquisition. The saturation frequency offset complex image data comprises voxels.

Execution of the machine-executable instructions further causes the processor to reconstruct a B0 map, a water image, and a fat image using the data for multiple echo shifts or echo times according to a Dixon-type MRI protocol. Execution of the machine-executable instructions further causes the processor to calculate a water phase angle using the water image and/or the fat image. Execution of the machine-executable instructions further causes the processor to calculate rotated complex image data by rotating the phase of the saturation frequency offset complex image data for each of the voxels using the water phase angle such that the complex water signal is aligned with the real axis for each voxel.

Execution of the machine-executable instructions further causes the processor to perform a B0 correction by calculating shifted complex image data using the rotated complex image data for each of the set of saturation frequency offsets and for each of the voxels using the B0 map. Execution of the machine-executable instructions further causes the processor to calculate a frequency dependent phase angle descriptive of the phase angle between the complex water signal and the complex fat signal for each of the set of saturation frequency offsets using a fat signal model comprising at least two fat species.

Execution of the machine-executable instructions further causes the processor to calculate a residual fat component correction factor by projecting the complex fat signal onto the real axis for each of the set of saturation frequency offsets and for each of the voxels using the frequency dependent phase angle. Execution of the machine-executable instructions further causes the processor to calculate a corrected water Z-spectrum image data by subtracting the correction factor for each of the set of saturation frequency offsets and for each of the voxels from the real component of the shifted complex image data.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a 'circuit,' 'module' or 'system'. Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, random access memory (RAM), read only memory (ROM), an optical disk, a magneto-optical disk, and the register file of the processor. Examples of optical disks include compact disks (CD) and digital versatile disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising a 'processor' should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as C or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the internet using an internet service provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE 488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, a tactile electronic display, a Braille screen, a cathode ray tube (CRT), a storage tube, a bi-stable display, an electronic paper, a vector display, a flat panel display, a vacuum fluorescent display (VF), light-emitting diode (LED) displays, an electroluminescent display (ELD), plasma display panels (PDP), a liquid crystal display (LCD), organic light-emitting diode displays (OLED), a projector, and a head-mounted display.

Magnetic Resonance (MR) data is defined herein as being the recorded measurements of radio frequency signals emitted by atomic spins using the antenna of a magnetic resonance apparatus during an MRI scan. MR data is an example of medical image data. An MR image is defined herein as being the reconstructed two or three dimensional visualization of anatomic data contained within the MRI data. This visualization can be performed using a computer. A Z-spectrum acquisition is magnetic resonance data that is suitable for reconstructing a Z-spectrum or image.

The water signal may be referred to as complex water signal herein and is interchangeable with when the water signal is part of or comprises a complex image or complex image data. The fat signal may be referred to as complex fat signal herein and is interchangeable with when the fat signal is part of or comprises a complex image or complex image data.

The term 'Z-spectrum acquisition for a set of saturation frequency offsets and at least one reference saturation frequency offset' herein refers to MR data which is suitable for processing into a Z-spectrum. The Z-spectrum acquisition for the set of saturation frequency offsets refers to the portion of the Z-spectrum data for a set of specific frequencies with for which saturation pulses were performed. The Z-spectrum acquisition for the at least one reference saturation frequency offset comprises data at one or more additional saturation frequency offsets that was also acquired and may be used to reconstruct a B0 map, a water image, and a fat image using a Dixon or Dixon-type MRI protocol.

The term 'saturation frequency offset complex image' in saturation frequency offset complex image data herein is a label for specific complex valued image data. 'Saturation frequency offset complex image data' may be replaced with 'first image data'.

The term 'rotated complex image' in rotated complex image data herein is a label for specific complex valued image data. 'Rotated complex image data' may be replaced with 'second image data'.

The term 'shifted complex image' in shifted complex image data herein is a label for specific complex valued image data. 'Shifted complex image data' may be replaced with 'third image data.'

The term 'water phase' in water phase angle is intended a label and 'water phase angle' may be replaced with 'first angle' herein.

The term 'saturation frequency offset dependent phase' in saturation frequency offset dependent phase angle is a label and may be replaced with 'second angle' herein.

The term 'residual fat component correction factor' is a label for a real valued number. 'Residual fat component correction factor' may be replaced with 'correction factor' herein.

BRIEF DESCRIPTION OF THE DRAWINGS

In the following preferred embodiments of the invention will be described, by way of example only, and with reference to the drawings in which:

FIG. 6 illustrates a multi-peak model of a fat spectrum;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
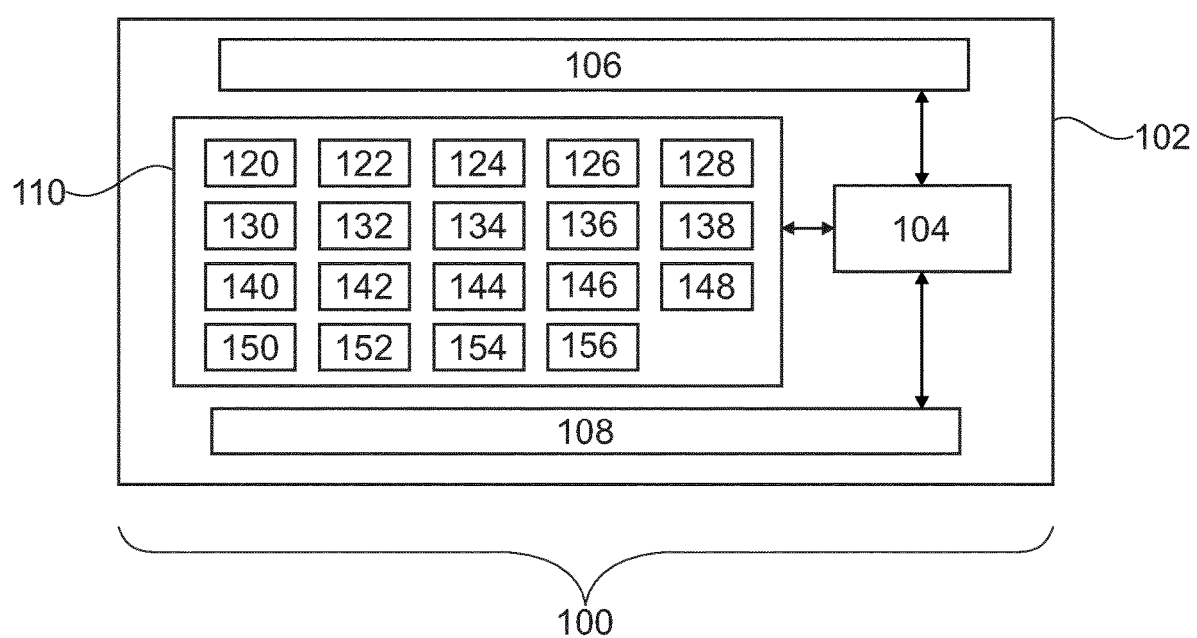
FIG. 1 illustrates an example of a medical imaging system.

FIG. 1 shows an example of a medical imaging system 100. The medical imaging system 100 comprises a computer 102. The computer comprises a processor 104 that is shown as being optionally connected to a hardware interface 106. The processor 104 is also optionally shown as being connected to a user interface 108. The processor 104 is shown as being connected to a memory 110. The memory 110 may be any combination of memory which is accessible to the processor 104. This may include such things as main memory, cached memory, and also non-volatile memory such as flash RAM, hard drives, or other storage devices. In some examples the memory 110 may be considered to be a non-transitory computer-readable medium.

The hardware interface 106 may for example be used for controlling other components of the medical imaging system 100 such as a magnetic resonance imaging system if one is available. The hardware interface 106 may also comprise network components so that the processor 104 can send and receive data via a computer network.

The memory 110 is shown as containing machine-executable instructions 120. The machine-executable instructions 120 enable the processor 104 to control other components of the medical imaging system 100 and/or to perform mathematical operations and/or image processing functions. The memory 110 is further shown as containing magnetic resonance imaging data 122 that is either received from an external source or system or from a component such as the magnetic resonance imaging system. The memory 110 is further shown as containing a Z-spectrum acquisition that is part of the magnetic resonance imaging data 122. The Z-spectrum acquisition 124 can be considered to be magnetic resonance data. The memory 110 is further shown as containing a set of saturation frequency offsets 126. This is a listing of frequencies for which saturation pulses were generated as part of the Z-spectrum acquisition.

The memory 110 is further shown as containing at least one reference saturation frequency offset 128. The memory 110 is further shown as containing a saturation frequency offset complex image data 130. The saturation frequency offset complex image data 130 comprises an image for each of the saturation frequency offsets that was reconstructed using the Z-spectrum acquisition. The memory 110 is further shown as containing a B0 map 132, a water image 134, and a fat image 136 that were reconstructed using the Z-spectrum acquisition 124 for the at least one reference saturation frequency offset 128. This was performed according to a Dixon magnetic resonance imaging protocol.

The memory 110 is shown as further containing a water phase angle 138. The water phase angle 138 is a phase angle which can be used to align the complex water signal in the saturation frequency offset complex image data 130 by rotation with the real axis in the complex plane such that the complex water signal becomes a real water signal. The water phase angle 138 is calculated using the water image 134 and/or the fat image 136. The memory 110 is further shown as containing rotated complex image data 140. The rotated complex image data is the saturation frequency offset complex image data 130 that has had its phase rotated by the water phase angle 138.

The memory 110 is further shown as containing shifted complex image data 142. The shifted complex image data 142 is calculated by using the B0 map to perform a B0 correction on the rotated complex image data 140. This has the effect of shifting the set of saturation frequency offsets 126. For example the rotated complex image data 140 and the shifted complex image data 142 may be in the form of a Z-spectrum image. The B0 correction may indicate a shift in the position of the saturation frequency offsets within the particular voxel.

The memory 110 is further shown as containing a frequency dependent phase angle 144. The frequency dependent phase angle 144 is descriptive of a phase angle between the complex water signal and the complex fat signal for each of the set of saturation frequency offsets that is calculated using a fat signal model. The fat signal model 146 is also shown as being stored in the memory 110. The fat signal model comprises a model which uses at least two fat species or peaks. By using multiple peaks, a more accurate value of the fat signal for a particular saturation frequency offset can be determined. The frequency dependent phase angle 144 is calculated for each of the set of saturation frequency offsets.

The computer memory is shown as containing optional measured fat signal model calibration data 148 that for example may have been received with the magnetic resonance imaging data 122. This for example may include measurements that were taken on a subject in different regions containing fat using different saturation frequency offsets. This for example may include measurements of various relaxation times using imaging or spectroscopy. In some examples the measured fat signal model calibration data is data which is the calibration.

The memory 110 is further shown as containing a residual fat component correction factor 150. The residual fat component correction factor is a projection of the complex fat signal onto the real axis in the complex plane. This is calculated using the shifted frequency dependent phase angle 144. This is done for each voxel and for each saturation frequency offset of the set of saturation frequency offsets 126. The memory 110 is further shown as containing a corrected water Z-spectrum image data 152 that was calculated by taking the real component of the shifted complex image data 142 and subtracting the residual fat component correction factor 150 from it. This also is performed for each voxel and for each saturation frequency offset of the set of saturation frequency offsets. The memory 110 is further shown as containing a fat corrected CEST magnetic resonance image 154 that was calculated from the corrected water Z-spectrum image data 152. In some instances the CEST protocol may be an APTw magnetic resonance imaging protocol. In this case the memory 110 is shown as containing an optional fat corrected APTw magnetic resonance image 156.

Figure 2:
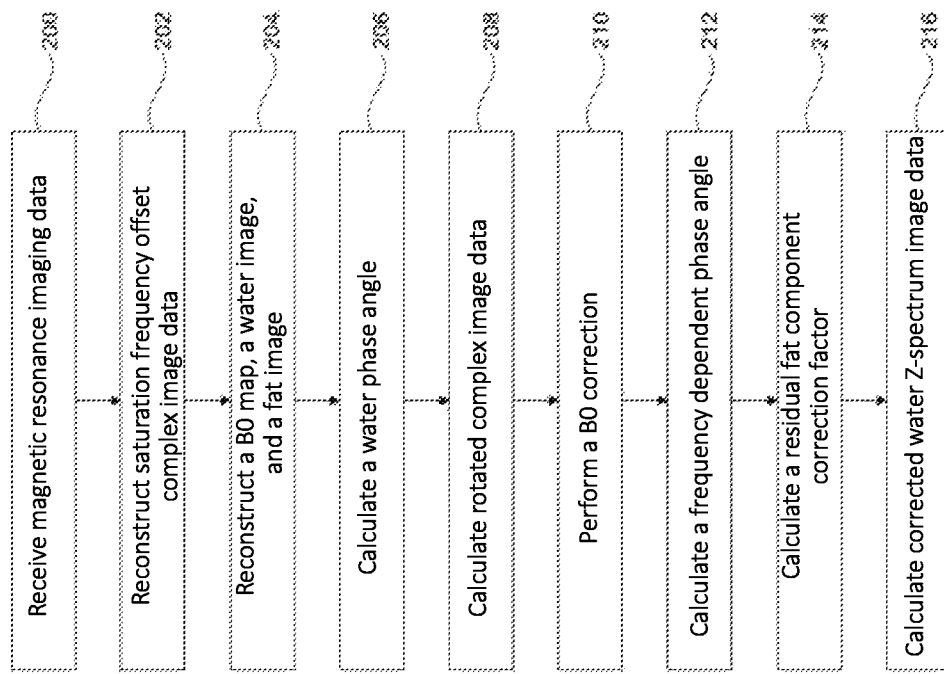
FIG. 2 shows a flow chart which illustrates a method of operating the medical imaging system of FIG. 1.

FIG. 2 shows a flowchart which illustrates a method of operating the medical imaging system 100 of FIG. 1. First in step 200 the medical imaging system 100 receives the magnetic resonance imaging data 122. Next in step 202 the saturation frequency offset complex image data 130 for each of the set of saturation frequency offsets 126 is reconstructed using the Z-spectrum acquisition 124. Then in step 204 the B0 map 132, the water image 134, and the fat image 136 are reconstructed using the Z-spectrum acquisition 124 for the at least one reference saturation frequency offset 128. Then in step 206 the water phase angle 138 is calculated using the water image 134 and/or the fat image 136. Next in step 208 the rotated complex image data 140 is calculated by rotating the phase of the saturation frequency offset complex image data 130 using the water phase angle 138.

Next in step 210 the shifted complex image data 142 is calculated by performing a B0 correction on the rotated complex image data 140. This is performed for each of the set of saturation frequencies and for each of the voxels. Next in step 212 the frequency dependent phase angle 144 is calculated using the fat signal model 146 and the set of saturation frequency offsets 126. The actual values of the set of saturation frequency offsets 126 may have been shifted by the B0 correction.

Next in step 214 the residual fat component correction factor 150 is calculated by projecting the complex fat signal onto the real axis in the complex plane for each of the set of saturation frequencies and for each of the voxels using the frequency dependent phase angle 144. Finally in step 216 the corrected water Z-spectrum image data 152 is calculated by subtracting the residual fat component correction factor 150 for each of the set of saturation frequency offsets 126 and for each of the voxels from the real component of the shifted complex image data 142.

Figure 3:
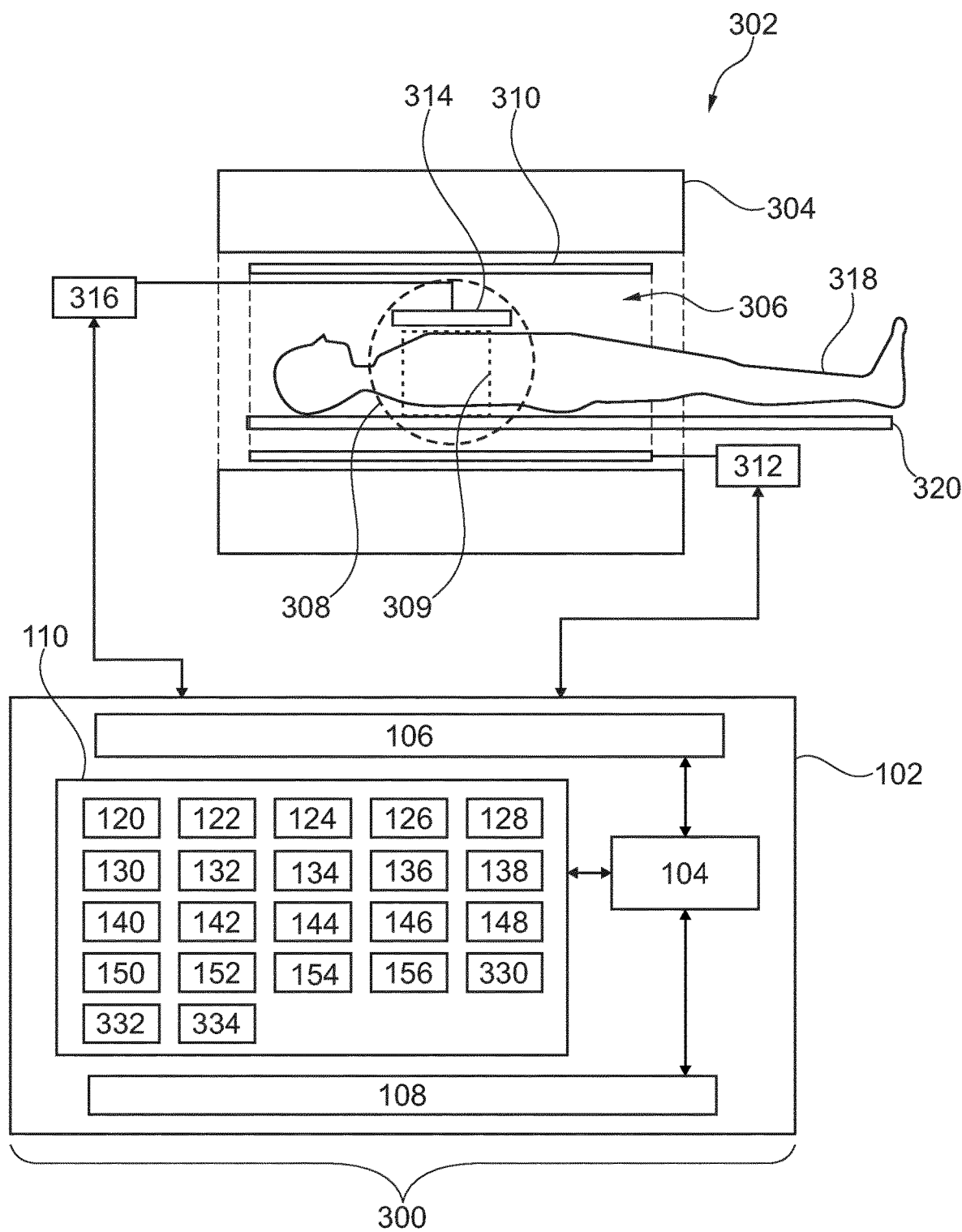
FIG. 3 illustrates a further example of a medical imaging system.

FIG. 3 illustrates a further example of a medical imaging system 300. The medical imaging system 300 in FIG. 3 is similar to the medical imaging system 100 in FIG. 1. The medical imaging system 300 in FIG. 3 is shown as additionally comprising a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging. A region of interest 309 is shown within the imaging zone 308. The magnetic resonance data is typically acquired for the region of interest. A subject 318 is shown as being supported by a subject support 320 such that at least a portion of the subject 318 is within the imaging zone 308 and the region of interest 309.

Within the bore 306 of the magnet there is also a set of magnetic field gradient coils 310 which is used for acquisition of magnetic resonance data to spatially encode magnetic spins within the imaging zone 308 of the magnet 304. The magnetic field gradient coils 310 are connected to a magnetic field gradient coil power supply 312. The magnetic field gradient coils 310 are intended to be representative. Typically magnetic field gradient coils 310 contain three separate sets of coils for spatial encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio frequency coil 314 is connected to a radio frequency transceiver 316. The radio frequency coil 314 and radio frequency transceiver 316 may be replaced by separate transmit and receive coils and a separate transmitter and receiver. It is understood that the radio frequency coil 314 and the radio frequency transceiver 316 are representative. The radio frequency coil 314 is intended to also represent a dedicated transmit antenna and a dedicated receive antenna. Likewise the transceiver 316 may also represent a separate transmitter and receiver. The radio frequency coil 314 may also have multiple receive/transmit elements and the radio frequency transceiver 316 may have multiple receive/transmit channels. For example if a parallel imaging technique such as SENSE is performed, the radio frequency could 314 will have multiple coil elements.

The transceiver 316 and the gradient controller 312 are shown as being connected to the hardware interface 106 of the computer system 102. The computer memory 110 is shown as additionally containing pulse sequence commands 330. The processor 104 can use the pulse sequence commands 330 to control the magnetic resonance imaging system 302 to acquire the magnetic resonance data 122. The memory 110 is shown as optionally containing fat signal model calibration pulse sequence commands 332. The fat calibration pulse sequence commands 332 are for example configured for measuring the line width and/or one or more relaxation rates of the two or more fat species. The computer memory 110 is further shown as containing calibration magnetic resonance data 334 that was acquired by controlling the magnetic resonance imaging system 302 with the fat calibration pulse sequence commands 332. The machine-executable instructions 120 may for example be used for calculating the optional measured fat signal model calibration data 148 from the calibration magnetic resonance data 334.

Figure 4:
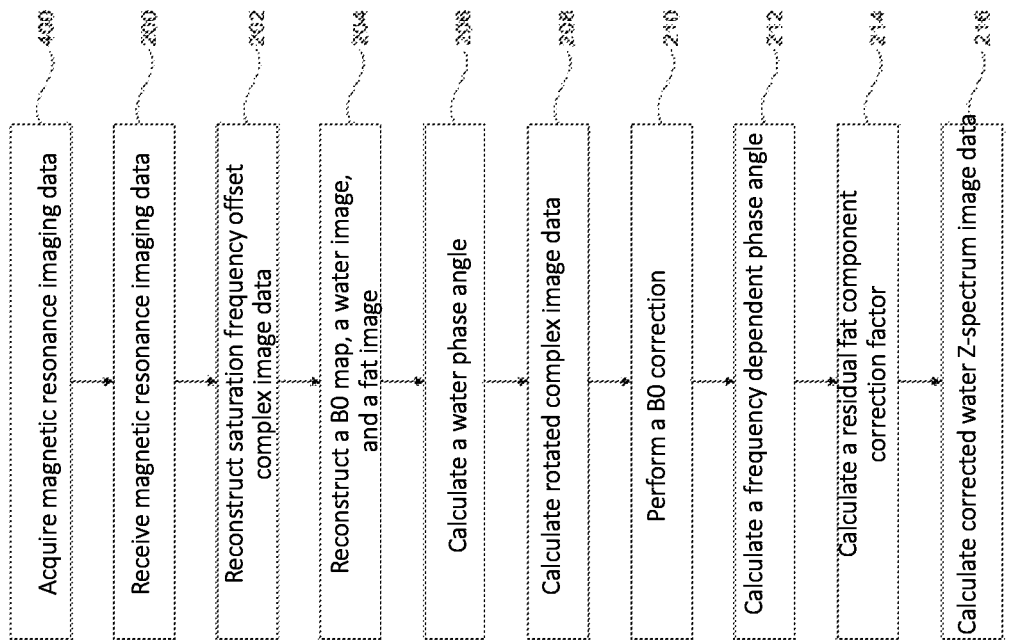
FIG. 4 shows a flow chart which illustrates a method of operating the medical imaging system of FIG. 3.

FIG. 4 shows a flowchart which illustrates a method of operating the medical imaging system 300 of FIG. 3. The method illustrated in FIG. 4 is similar to the method illustrated in FIG. 2. The method in FIG. 4 starts with step 400. In step 400 the pulse sequence commands 330 are used to acquire the magnetic resonance imaging data 122. After step 400 the method proceeds to step 200 of the method of FIG. 2 and the method is thereafter identical with the method illustrated in FIG. 2.

The methods illustrated in FIGS. 2 and 4 may for example be implemented by the machine-executable instructions 120 as is illustrated in FIGS. 1 and 3.

Examples may provide for an MRI technique to obtain an accurate assessment of the magnetization transfer asymmetry ($MTR_{asym}$), which for instance is displayed as amide proton transfer-weighted (APTw) or CEST image, in the presence of fat. This technique may comprise an MR image acquisition, a spectral fat saturation model, and a processing procedure. The image acquisition involves a complex Z-spectrum acquisition with non-zero echo shifts, leading to suitable phase differences between the complex water signal and the complex fat signal. One Z-spectrum acquisition serves as reference to determine the water signal, the fat signal, and the magnetic field inhomogeneity (B0) via a standard Dixon method. $MTR_{asym}$ of the water signal is derived from the real part of the complex Z-spectrum in multiple steps: (a) complex rotation of all Z-spectrum images based on the water signal, the fat signal, and the magnitude of the reference acquisition, (b) interpolation along the saturation frequency offset dimension for B0 correction, (c) subtraction of a projection of the imaginary part (representing the fat signal) from the real part, using a model for the saturation frequency offset dependent phase angle between the water signal and the fat signal, (d) calculation of $MTR_{asym}$ from the fat corrected real part of the Z-spectrum, which represents the pure, partly saturated water signal.

APT is a technique for MR-based molecular imaging of endogenous cytosolic proteins or peptides. It is based on the CEST effect and reflects protein concentrations as well as local pH via the exchange rate. Promising clinical applications of APT MRI are envisioned in oncology (enhanced protein concentrations in tumors, differentiation of radiation necrosis and active or recurrent tumors) and in neurology (ischemic acidosis in stroke). The detection of amide protons is based on $MTR_{asym}$ analysis on the water signal using symmetric radio frequency saturation frequency offsets ω (±3.5 ppm) around the water resonance, while the APTw signal is found as image signal reduction around +3.5 ppm. Measuring the asymmetry of the signal amplitude as function of the saturation frequency offset is inherently very sensitive to confounding signal contributions around −3.5 ppm, overlapping with the chemical shift range of fat signals. Fat signals may particularly influence APTw imaging in fat containing tissues or via partial volume effects, when voxels are chosen close to water-fat interfaces. Typically, fat suppression pulses (e.g. SPIR) are used in common APTw or CEST MRI sequences to accommodate for this problem.

Figure 5:
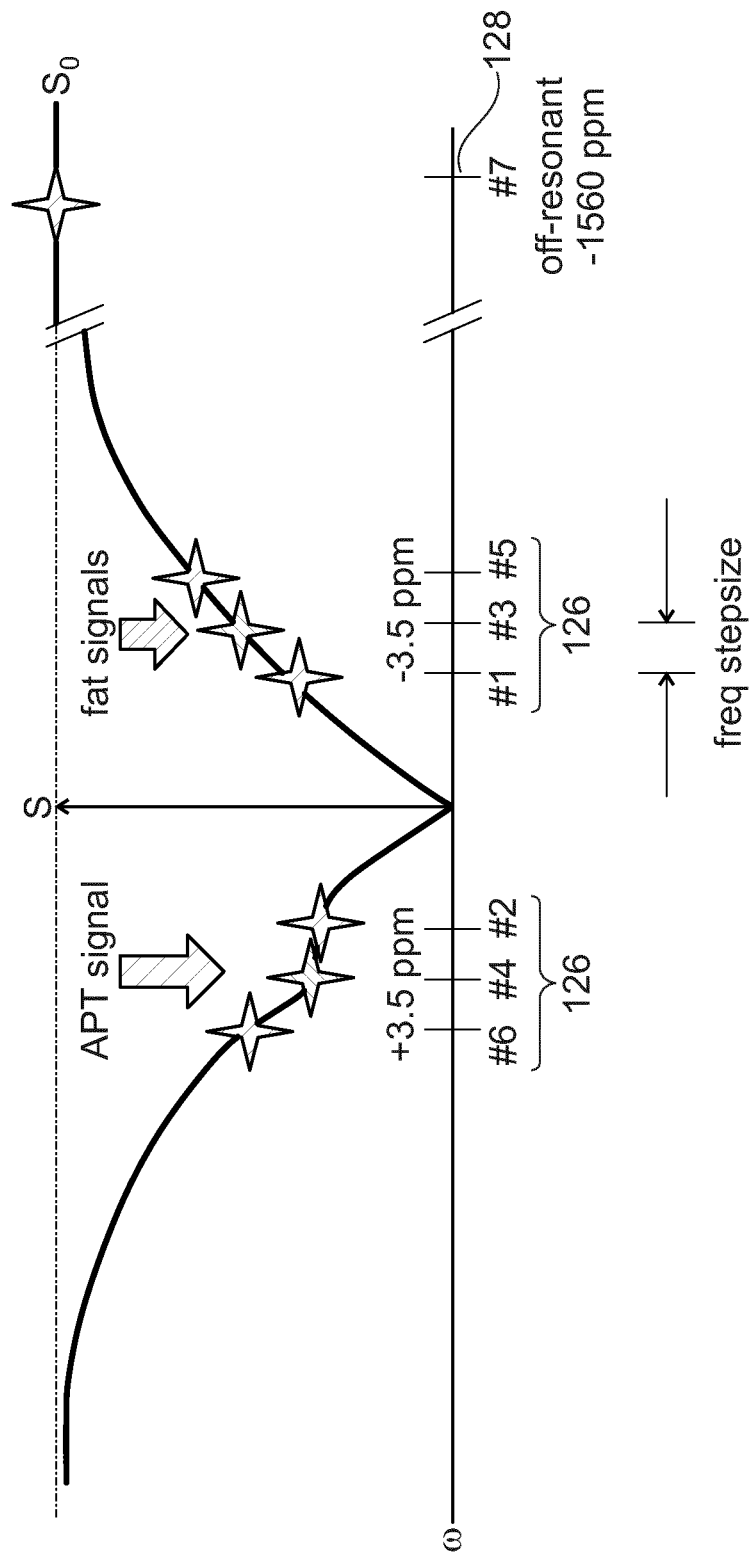
FIG. 5 shows a Z-spectrum and illustrates an example APTw acquisition scheme.

An example APTw image acquisition scheme is shown in FIG. 5. Multiple images S[ω] are recorded with variable saturation frequency offset ω—so called Z—spectrum—needed for a $B_0$ field homogeneity corrected and normalized ($S_0$) assessment of $MTR_{asym}=(S[-\omega]-S[+\omega])/S_0$. The example APTw image acquisition scheme uses 7 acquisitions at different saturation frequency offsets ω. Positions 1, 2, 3, 4, 5, and 6 correspond to the set of saturation frequency offsets 126. Position 7 corresponds to the at least one reference saturation frequency offset 128.

Examples May Overcome One or More of the Following Technical Problems

Small imperfections in fat suppression, barely visible on anatomical water and fat images, may lead to significant deviations in the $MTR_{asym}$ analysis, which is designed to accurately detect small signal changes typically in the range of 0-10% of $S_0$. While fat suppression is mostly accurate for APT applications in the brain (no fat content), it often fails for body applications because of the closely located water and fat compartments (e.g. breast MRI) or because of partial fat content of the tissue (e.g. liver MRI).

Fat suppression pulses reduce the contrast to noise (per unit scan time) because Water Signals are Partly Suppressed Fat suppression pulses take some time between the end of RF saturation and the image acquisition sequence, thus leading to some decay of APT/CEST contrast (T1 relaxation)

Fat suppression pulses may introduce errors in $MTR_{asym}$ analysis in partially fat containing voxels, because of an interaction of the saturation pulse and the fat suppression pulse for Z-spectrum acquisitions around ω=−3.5 ppm, leading to imperfect fat suppression or to a modified saturation level.

Alternatively, Dixon-type water-fat separation could be used for each Z-spectrum acquisition S[ω]. However, this may have several disadvantages:

Multiple echo shifts (e.g. 2 or 3) are needed to separate water and fat for each S[ω]. This may largely prolong the scan time, e.g. in multi-acquisition Dixon fast or turbo spin echo scans.

Around S[ω=−3.5 ppm], the fat signal is (partly) saturated by the saturation pulses, which is not taken into account in standard Dixon-type water-fat separation algorithms. This typically leads to errors in the water-fat separation in this range of saturation frequency offsets.

Examples may incorporate all or part of the following acquisition and processing procedure to obtain an accurate assessment of $MTR_{asym}$ from the water signal in case of arbitrary water-fat signal contributions in each voxel:

Image Acquisition/Reconstruction

Z-spectrum data is acquired and the full complex image data Re[ω,x] and Im[ω,x] is obtained in each voxel location x.

Each saturation frequency offset complex image is acquired once with the same echo shift ES (spin echo)/echo time TE (gradient echo), where the complex water signal and the complex fat signal are neither in-phase nor out-of-phase.

One positive or largely detuned saturation frequency offset $\omega_{ref}$ is selected, called reference saturation frequency offset, which is acquired at least one more time with different ES or TE.

From this reference acquisition, a $B_0$ map, a water image ($W_r$), and a magnitude image ($S_r$) are calculated, e.g. using any (standard) multi-point Dixon technique. A fat image ($F_r$) is calculated optionally in addition.

Spectral Fat Saturation Model

A spectral fat model, describing the resonance frequency offset and the relative resonance area of each of a set of fat species, is used to calculate a fat saturation spectrum $F_{sat}[\omega]$.

For each saturation frequency offset, at which individual fat species may be (partly) saturated, a vector summation depending on the chosen ES/TE is carried out to derive the actual frequency dependent phase angle $\alpha[\omega]$ between the complex water and the complex fat signal.

Processing

Correct the full complex image data at each $\omega$ using a complex rotation $\varepsilon[x]$ in each voxel location x, such that the complex water signal is aligned with the real axis in the complex plane. $\varepsilon[x]$ is derived from the reference acquisition using the water signal and equally applied to all Z-spectrum acquisitions $\omega$. The obtained corrected complex Z-spectrum is termed $Re'[\omega,x]$, $Im'[\omega,x]$.

Use the $B_0$ map from the reference acquisition to separately shift and interpolate $Re'[\omega,x]$ and $Im'[\omega,x]$ for $B_0$ correction in each voxel.

In each voxel, correct the real part of the Z-spectrum to only contain water signal, $Re_{FC}[\omega,x]$. This is done by subtracting the projection of the complex fat signal on the real axis in the complex plane, the projection depending on the phase angle $\alpha[\omega]$ from (2.b). Finally normalize to $S_0$.

Calculate a fat signal corrected $MTR_{asym,FC}[\omega,x]$ from $Re_{FC}$, e.g. used as fat signal corrected APTw image=$MTR_{asym,FC}[\omega=+3.5\ ppm, x]$.

Examples may contain one or more of the following features:

Image acquisition/reconstruction

Acquire Z-spectrum data and obtain the full complex image data $Re[\omega,x]$ and $Im[\omega,x]$.

Each saturation frequency offset image is acquired once with the same echo shift $ES_1$ (SE, FSE, SE-EPI, ...) or echo time $TE_1$ (GRE, SSFP, ...), leading to an overall phase difference between the complex water signal and the complex fat signal of preferably about $\alpha=90°$. In general, any phase difference could be used, which is neither in-phase (0°) nor out-of-phase (180°).

For example, a Z-spectrum is acquired with a single-shot FSE (fast spin echo) readout using an echo shift (time shift of the data acquisition window with respect to the spin echo) of $ES_1=-0.52$ ms at 3 T. The FSE readout is repeated with a saturation pulse, e.g. consisting of a quasi CW train of 50 ms sinc-gaussian pulse elements with a total duration of 2 s and a $B1_{rms}$ power of 2 µT, at 43 different saturation frequency offsets $\omega=\pm0.44, \pm0.88, \ldots, \pm9.2$ ppm (frequency step size 0.44 ppm) and $\omega_{ref}=-1560$ ppm ($S_0$).

Alternatively, in particular for APTw imaging, seven different frequency offsets are measured with $\omega=\pm2.72$, $\pm3.50$, $\pm4.28$ ppm (frequency step size 0.78 ppm) and $-1560$ ppm.

One saturation frequency offset $\omega_{ref}$ is selected, called reference saturation frequency offset, with which a reference acquisition is performed at least one more time with a different ES or TE. This should preferably be either $S_0$ (no saturation or a largely detuned $\omega$, e.g. $\omega=-1560$ ppm) or $S[+3.5\ ppm]$ (particularly for APT). Any other $S[\omega_{ref}]$ could be chosen, as long as co is positive and preferably $\omega>+2$ ppm (where there is no influence of any fat signals).

For example, in addition to the FSE acquisition with $ES_1=-0.52$ ms, two further acquisitions are made with $ES2=0$ ms and $ES3=+0.52$ ms.

A possible variant is to skip (1.c) and to use only one acquisition at $\omega_{ref}$ (from 1.b) and to apply a single-point Dixon reconstruction as described in (1.d).

From the reference acquisition (1.c), a $B_0$ map, a water image ($W_r$) and a magnitude image ($S_r$) are calculated, e.g. using any (standard) multi-point Dixon technique. A fat image ($F_r$) is calculated optionally.

Spetral Fat Saturation Model

A spectral fat model, describing the resonance frequency offset and the relative resonance area of each of a set of fat species, is used to calculate a fat saturation spectrum $F_{sat}[\omega]$.

For each saturation frequency offset, at which individual fat species may be (partly) saturated, a vector summation depending on the chosen ES/TE is carried out to derive the actual frequency dependent phase angle $\alpha[\omega]$ between the complex water signal and the complex fat signal.

FIG. 6 gives an example of a fat signal model 600 and the derived frequency dependent phase angle $\alpha[\omega]$ 602, for a specific echo shift of ES=$-0.52$ ms. The overall complex fat signal is first calculated without saturation effect (2.a) using known fat signal frequencies $\omega_{F,i}$, weights $p_i$, and echo shift ES/phase angle $\alpha_i$ according to $$\alpha_i = 2\pi \cdot ES \cdot \omega_{F,i} \quad (1)$$

$$F = |F|e^{i\alpha} = \sum_{i=1}^{N} p_i e^{i\alpha_i} \quad (2)$$

The argument of F provides the total phase angle $\alpha$ between the complex water signal and the complex fat signal. The spectral fat saturation model is completed by introducing Lorentz-shaped weights $L_i$, normalized to $L_i[\omega_{F,i}]=1$, with a suitable linewidth A (e.g. $\Delta=1$ ppm) as function of the saturation frequency offset $\omega$:

$$F_{sat}[\omega] = \sum_{i=1}^{N} p_i(1-L_i[\omega])e^{i\alpha_i} \quad (3)$$

$$L_i[\omega] = \frac{\Delta^2}{4(\omega-\omega_{F,i})^2 + \Delta^2} \quad (4)$$

The phase angle as function of the saturation frequency offset is finally calculated as the argument of $F_{sat}[\omega]$:

$$\alpha[\omega] = atan(Im[F_{sat}], Re[F_{sat}]) \quad (5)$$

Figure 7:
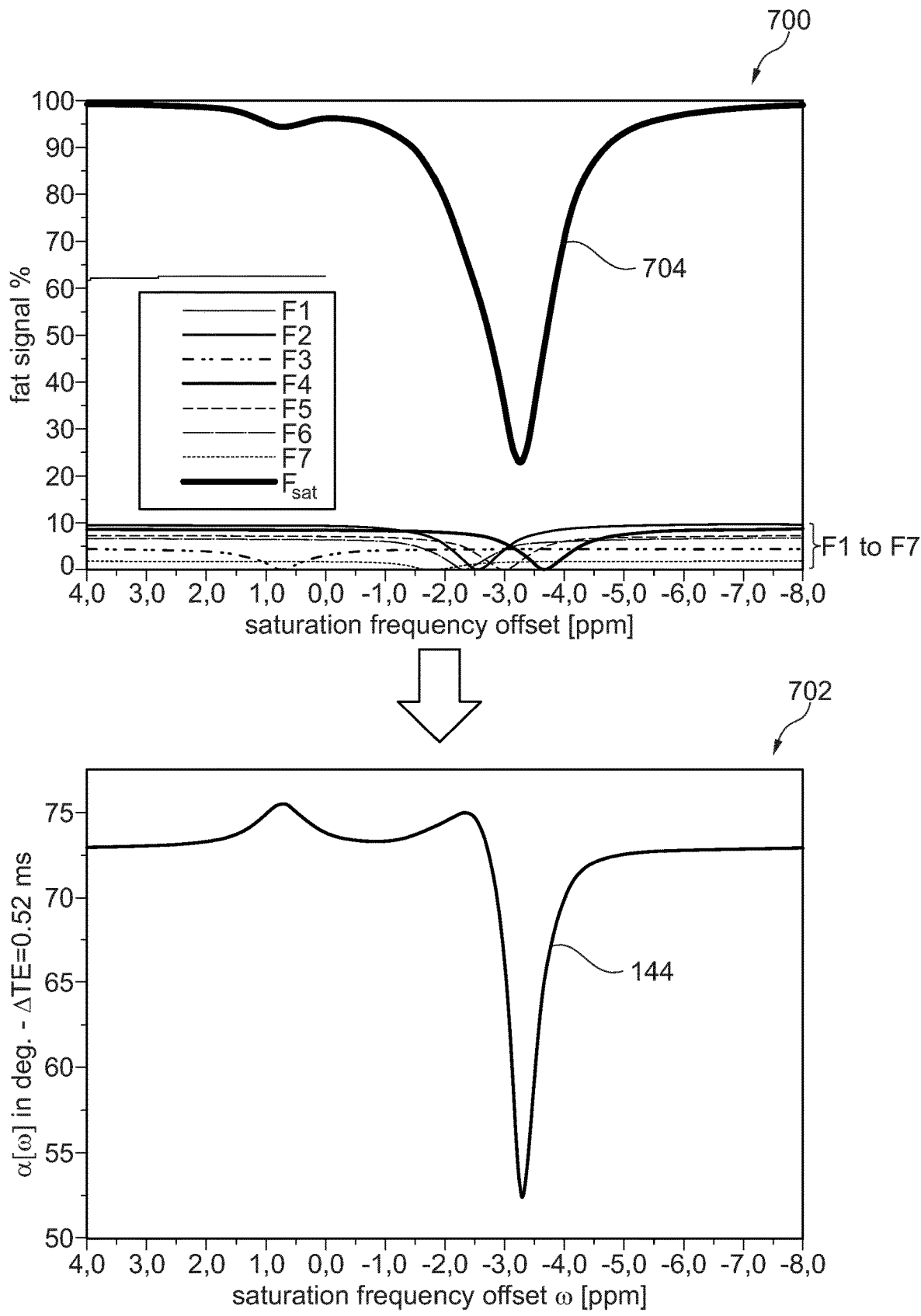
FIG. 7 illustrates a model of the saturation of the individual fat species and a derived frequency dependent phase angle.

FIG. 7 shows two plots. Plot 700 shows the fat signal calculated from the fat signal model versus the saturation frequency offset in ppm. At the bottom of the plot are shown the components for each of the peaks considered in this example. The curve above is the sum of the components 704. Plot 702 shows the value of the frequency dependent phase angle $\alpha[\omega]$ 144 in ppm.

Processing

Complex Rotation

The full complex image data at each co is corrected in this processing step using a complex rotation $\varepsilon[x]$ in each voxel location x, such that the complex water signal W is aligned with the real axis in the complex plane.

If $W_r$ from the reference acquisition (1.c) at $\omega_{ref}$ is known as complex number based on the Dixon reconstruction, $\varepsilon[x]$ can be immediately obtained by the phase angle $\varepsilon[x]=\text{atan}(\text{Im}[W_r], \text{Re}[W_r])$. Otherwise, $\varepsilon[x]$ can be derived, using the magnitude $W_r$ of the complex water signal (water image) and the overall magnitude $S_r$ (water+fat):

$$\varepsilon[x] = \alpha_r - \varphi_r[x] - \arcsin\left[\frac{W_r}{S_r}[x] \cdot \sin(\pi - \alpha_r)\right] \qquad (6)$$

$$\varphi_r = \text{atan}(\text{Im}[\omega_{ref}, x], \text{Re}[\omega_{ref}, x]) \qquad (7)$$

$$\alpha_r = \alpha[\omega_{ref}] \qquad (8)$$

Optionally (e.g in regions of largely dominating fat signal), $\varepsilon[x]$ can also be derived from the fat signal:

$$\varepsilon[x] = -\varphi_r[x] + \arcsin\left[\frac{F_r}{S_r}[x] \cdot \sin(\pi - \alpha_r)\right] \qquad (6')$$

The actual complex rotation is obtained using the standard formula for each voxel location x, using identical rotation angles $\varepsilon[x]$ at each saturation frequency offset $\omega$:

Re'[ω,x]=cos(ε[x])·Re[ω,x]−sin(ε[x])·Im[ω,x]

Im'[ω,x]=sin(ε[x])·Re[ω,x]+cos(ε[x])·Im[ω,x]  (9)

Equation (6) for $\varepsilon$ is derived using the sinus theorem:

$$\frac{S_r}{\sin\delta} = \frac{W_r}{\sin\gamma} \qquad (6a)$$

$$\delta = \pi - \alpha_r \qquad (6b)$$

$$\gamma = \alpha_r - \varepsilon - \varphi_r \qquad (6c)$$

$$\Rightarrow \sin(\alpha_r - \varepsilon - \varphi_r) = \frac{W_r}{S_r}\sin(\pi - \alpha_r) \qquad (6d)$$

Figure 8:
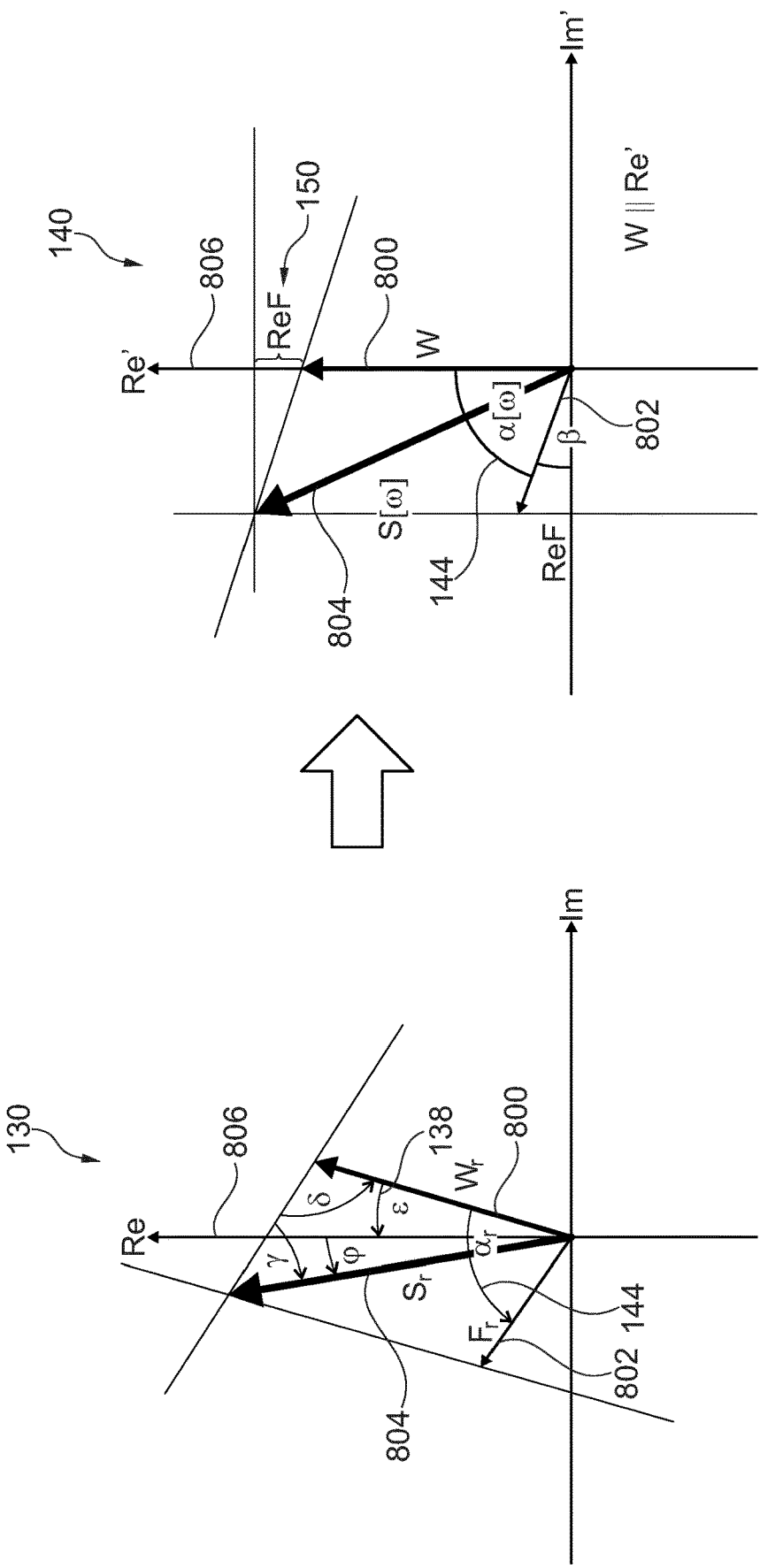
FIG. 8 shows representations of the water and fat signals in the complex plane.

FIG. 8 shows two plots. The one labeled 130 illustrates the water signal $W_r$ 800, the fat signal $F_r$ 802, and the overall magnitude $S_r$ 804 in the complex plane in one voxel of the saturation frequency offset complex image data 130. The water phase angle 138 and the frequency dependent phase angle 144 are also shown.

The other plot labeled 140 shows an example of rotated complex image data 140, where the water phase angle 138 was used to rotate the phase of the complex image data 130. It can be seen that the water signal 800 is now aligned with the real axis 806 in the complex plane. The plot also illustrates how the residual fat component correction factor 150 is a projection of the complex fat signal 802 onto the real axis 806 in the complex plane. The actual water signal 800 is obtained by subtracting from the projection of the magnitude 804 onto the real axis 806 the residual fat component correction factor 150.

Equation (6') for $\varepsilon$ is derived in analogy:

$$\frac{S_r}{\sin\delta} = \frac{F_r}{\sin(\varphi_r + \varepsilon)} \qquad (6'a)$$

$$\sin(\varphi_r + \varepsilon) = \frac{F_r}{S_r}\sin(\pi - \alpha_r) \qquad (6'b)$$

As $\varepsilon$ does not depend on water or fat saturation (which only changes the magnitudes of W and F but not the angle between W and the real axis), the correction derived from the reference acquisition can be equally applied to all Z-spectrum acquisitions (as long as they are acquired with the same ES/TE), such that all complex W signals will be aligned with the real axis for any ω after this processing step.

b1. Optional Further Correction of the $B_0$ Map

Precise information on the magnetic field inhomogeneity on a level of 0.1 ppm or better is essential for precise determination of $MTR_{asym}$. In some cases, the accuracy of the B0 maps may be compromised particularly in the presence of fat. Fat saturation shift referencing, here termed FASSR, in analogy to the known water saturation shift referencing (WASSR) technique, is applicable, if sufficient Z-spectrum information is obtained around the saturation frequency offset, where the largest fat saturation is observed. Then, in each voxel, the frequency value at the largest fat saturation can be determined by a minimum search or via fitting of a fat saturation spectrum. If this saturation frequency is indicating a different magnetic field inhomogeneity as compared to the $B_0$ map, the $B_0$ values may be corrected based on the observed fat saturation shift (or even fully replaced by the observed fat frequency shift values).

b. $B_0$ Correction of Complex Z-Spectrum Data Re'[ω,x] and Im'[ω,x]

Due to local magnetic field inhomogeneity $B_0$ the complex Z-spectrum Re'/Im' needs to be reconstructed for actual target saturation frequency offsets in each voxel. When Re and Im denote the true Z-spectrum without $B_0$ shift effects, the following relation holds:

$$\text{Re'}[\omega,x] = \text{Re}[\omega - B_0(x), x] \qquad (10)$$

$$\text{Im'}[\omega,x] = \text{Im}[\omega - B_0(x), x] \qquad (11)$$

For $B_0$ correction, an interpolation of the signal acquired at neighbouring saturation offset frequencies is applied to approximate Re/Im:

$$\text{Re}[\omega,x] = \Sigma_i \lambda_{Re,i}[\omega,x]\text{Re}'[\omega_i,x] \qquad (12)$$

$$\text{Im}[\omega,x] = \Sigma_i \lambda_{Im,i}[\omega,x]\text{Im}'[\omega_i,x] \qquad (13)$$

where $\lambda_{Re,i}/\lambda_{Im,i}$ are the interpolation coefficients, which for example can be defined via Lagrangian interpolation terms:

$$\lambda_{Re,i}[\omega] = \prod_{k=0\ldots i-1, i+1\ldots p} \frac{\omega - u_k}{u_i - u_k} \qquad (14)$$

$$\lambda_{Im,i}[\omega] = \prod_{k=0\ldots i-1, i+1\ldots p} \frac{\omega - u_k}{u_i - u_k} \qquad (15)$$

With $$u_i = \omega_i - B_0(x) \qquad (16)$$

For the simplicity of notation, Re and Im have been redefined as Re=Re"/Im=Im" here.

Figure 9:
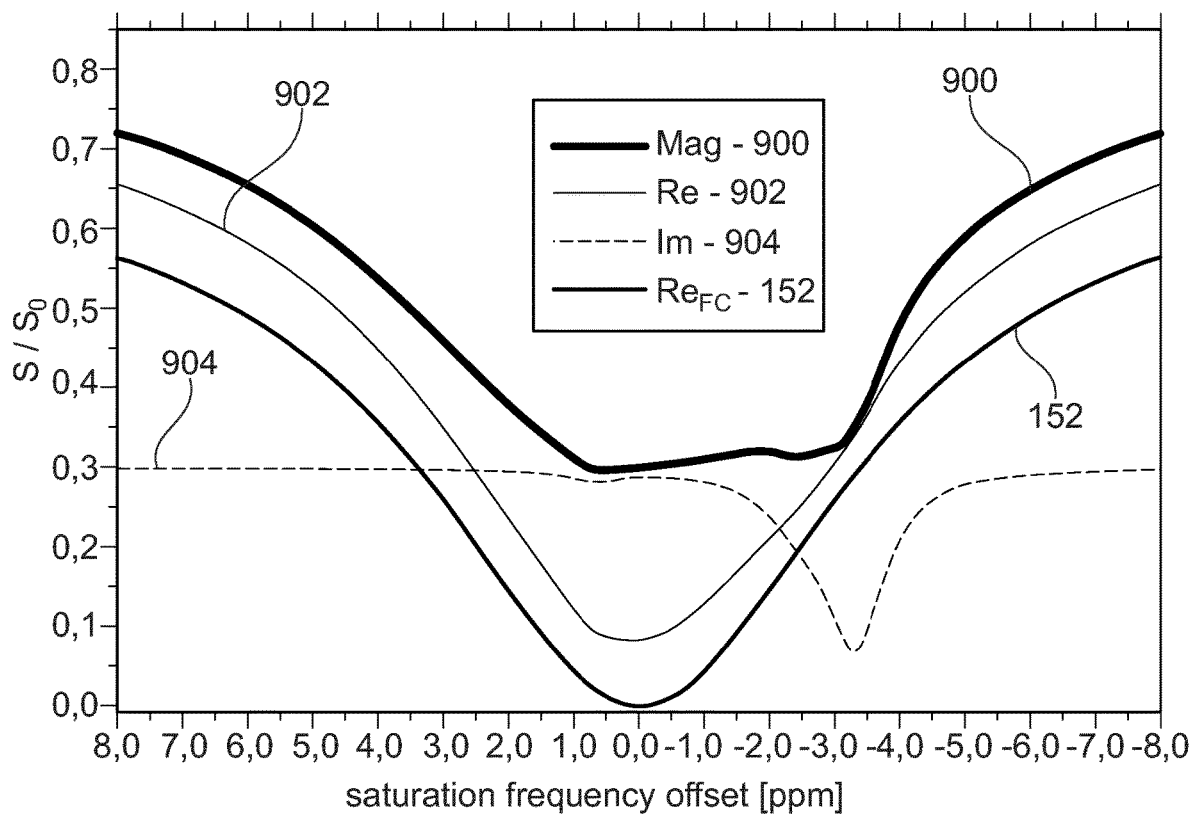
FIG. 9 shows example Z-spectra obtained after correction steps for a voxel containing 70% water and 30% fat.

After the $B_0$ correction, the complex Z-spectrum is (approximately) centered around 0 ppm for all voxels. This is illustrated in FIG. 9 for a voxel that contains 70% water and 30% fat. The line marked 900 and also mag represents a standard magnitude Z-spectrum. The lines labeled 902 and 904 are the real and the imaginary components of a corrected complex Z-spectrum after processing, respectively. The line labeled 152 represents the final, fat corrected water Z-spectrum.

Fat Correction for the Real Part of the Complex Z-Spectrum

In each voxel, the real part $\text{Re}[\omega,x]$ of the $B_0$-interpolated Z-spectrum is corrected using the fat spectrum stored in $\text{Im}[\omega,x]$ and the fat saturation model $\alpha[\omega]$ such that a pure water signal is obtained. The corrected real part is termed $\text{Re}_{FC}[\omega]$. This is done by subtracting the projection of the complex fat signal on the real axis in the complex plane, the projection depending on the phase angle $\alpha[\omega]$. Finally, a normalization to $S_0$ is performed:

$$\text{Re}_{FC}[\omega, x] = \frac{1}{S_0}\left[\text{Re}[\omega, x] - I[\omega, x] \cdot \tan\left(\frac{\pi}{2} - \alpha[\omega]\right)\right] \quad (17)$$

This formula is similar to a single-point Dixon method for extracting the water signal, but used here for a full Z-spectrum analysis in combination with the frequency dependent phase angle $\alpha[\omega]$.

Equation (17) is explained by considering plot 140 in FIG. 8, where $\text{Re}_{FC}$ is representing the water signal amplitude W and ReF denotes the projection of the complex fat signal on the real axis in the complex plane:

$W = \text{Re} - \text{ReF}$ (17a)

$= \text{Re} - \text{Im} \cdot \tan(\beta)$ (17b)

$= \text{Re} - \text{Im} \cdot \tan(\pi/2 - \alpha)$ (17c)

Finally, the fat corrected $\text{MTR}_{asym,FC}$ is calculated from $\text{Re}_{FC}$: $\text{MTR}_{asym,FC}[\omega, x] = \text{Re}_{FC}[\omega, x] - \text{Re}_{FC}[+\omega, x]$ As an example, a fat corrected APTw image can be immediately obtained from $\text{MTR}_{asym,FC}$ at +3.5 ppm:

$\text{APTw}_{FC}[x] = \text{MTR}_{asym,FC}[+3.5 \text{ ppm},x]$.

Figure 10:
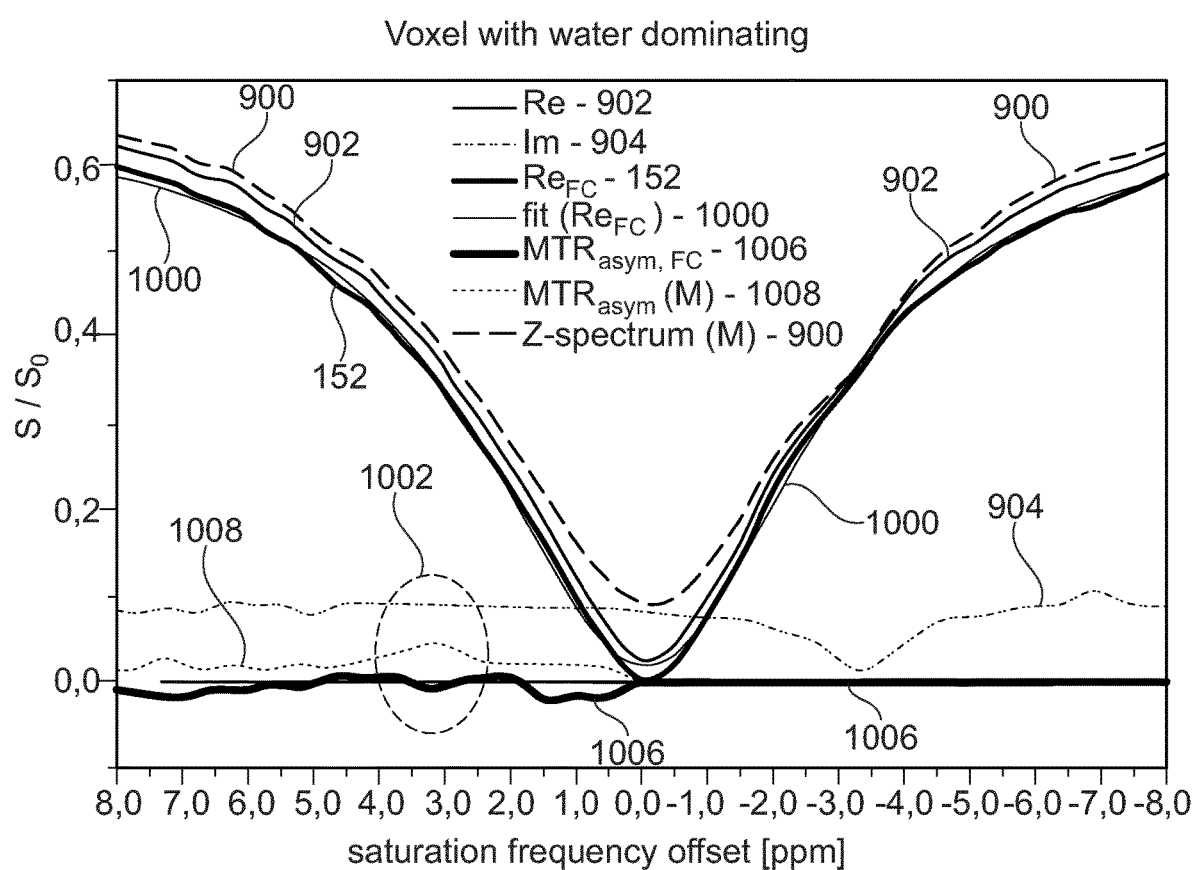
FIG. 10 shows example Z-spectra for abdominal APTw imaging with fat correction for a voxel containing mostly water.

FIG. 10 illustrates an example of a Z-spectrum for a voxel that is dominated by water. There is therefore no or minimal amount of fat to corrupt the standard Z-spectrum 900. A symmetric model function 1000 is fit to the corrected water Z-spectrum 152 in this case. The circle 1002 shows the region of the spectrum relevant for APTw imaging. Curve 1008 shows the $\text{MTR}_{asym}$ values calculated using the standard magnitude curve 900. Curve 1006 shows the $\text{MTR}_{asym}$ values calculated using the curve 152.

Figure 11:
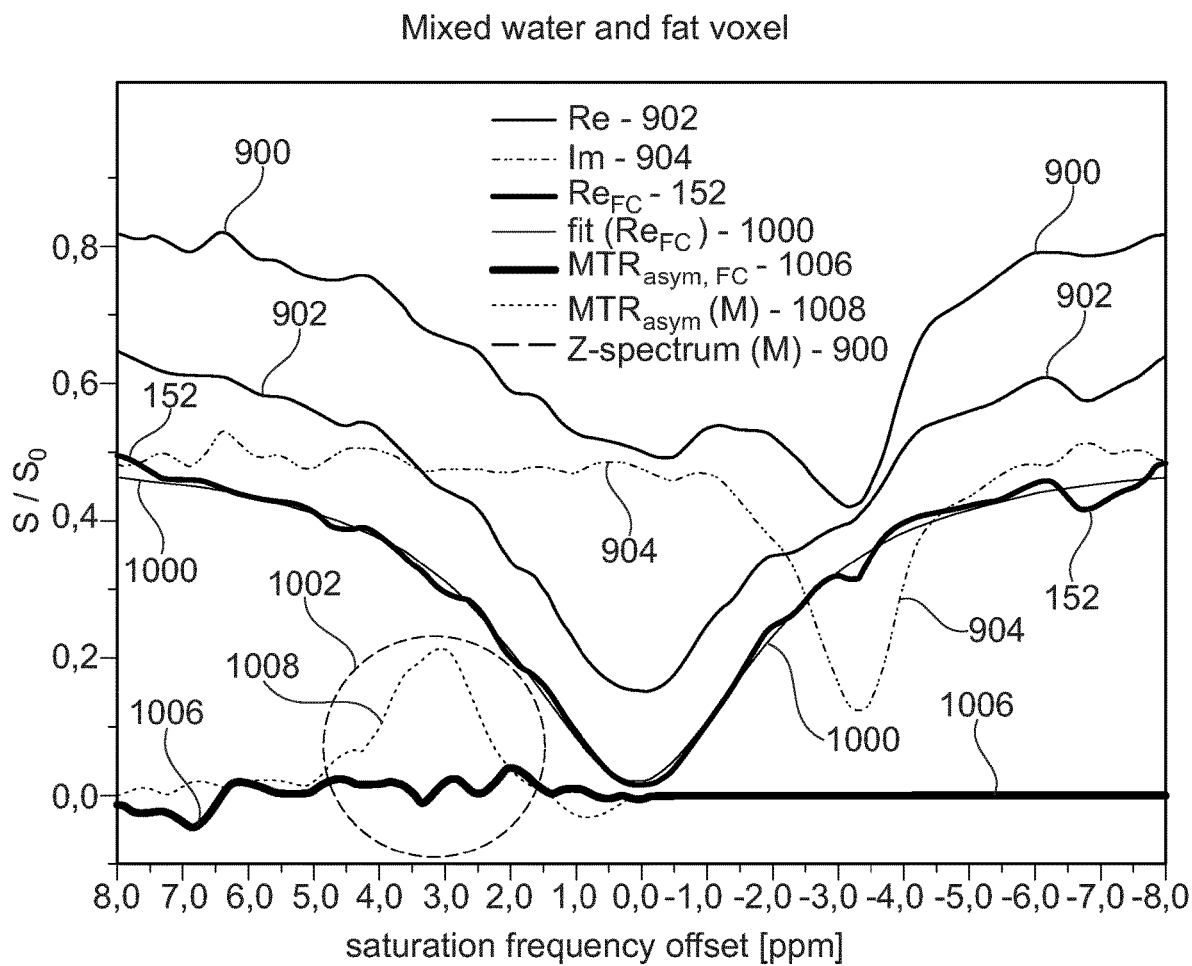
FIG. 11 shows example Z-spectra for abdominal APTw imaging with fat correction for a voxel containing about equal contributions of water and fat.

FIG. 11 shows the same plot as FIG. 10 except for that the voxel contains mixed water and fat. It can be seen that the curve 1006 in both FIGS. 10 and 11 is very similar. However, in FIG. 11 the curve 1008 is much worse than it is in FIG. 10.

Figure 12:
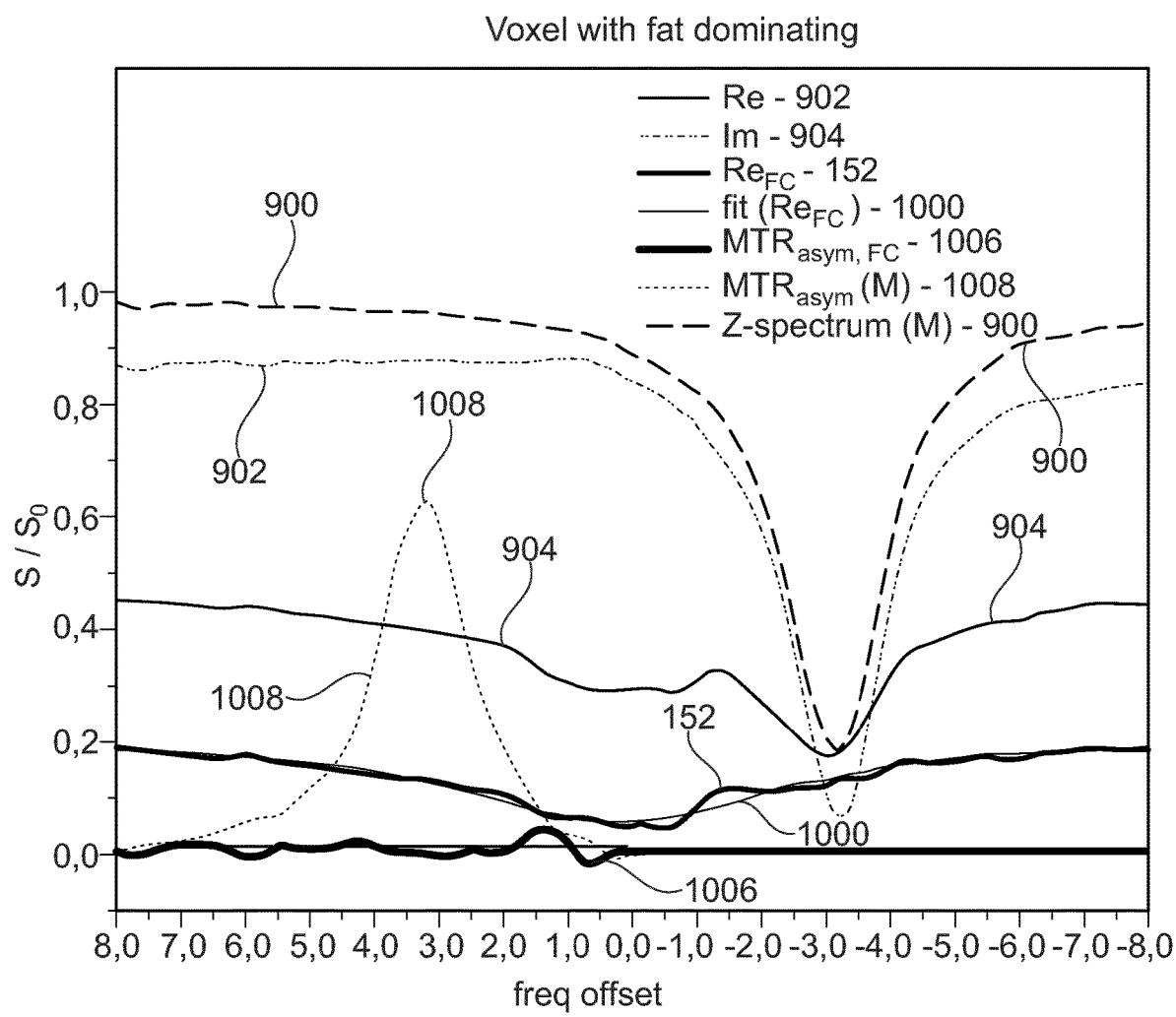
FIG. 12 shows example Z-spectra for abdominal APTw imaging with fat correction for a voxel containing mostly fat.

FIG. 12 shows the same plot as in FIGS. 10 and 11 but for a voxel that is dominated by fat. The signal 1008 can be seen as totally dominating the region applicable for APTw.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the internet or other wired or wireless telecommunication systems. Any reference signs in the claims should not be construed as limiting the scope.

LIST OF REFERENCE NUMERALS 100 medical imaging system
102 computer
104 processor
106 hardware interface
108 user interface
110 memory
120 machine executable instructions
122 magnetic resonance imaging data
124 Z-spectrum acquisition
126 set of saturation frequency offsets
128 at least one reference saturation frequency offset
130 saturation frequency offset complex image data
132 B0 map
134 water image
136 fat image
138 water phase angle
140 rotated complex image data
142 shifted complex image data
144 frequency dependent phase angle
146 fat signal model
148 optional measured fat signal model calibration data
150 residual fat component correction factor
152 corrected water Z-spectrum image data
154 fat corrected CEST magnetic resonance image
156 fat corrected APTw magnetic resonance image
200 receive magnetic resonance imaging data
202 reconstruct saturation frequency offset complex image data for each of the set of saturation frequency offsets from the Z-spectrum acquisition
204 reconstruct a B0 map, a water image, and a fat image from the Z-spectrum acquisition at the at least one reference saturation frequency offset with multiple echo shifts or echo times according to a Dixon-type magnetic resonance imaging protocol
206 calculate a water phase angle using the water image and/or the fat image
208 calculate rotated complex image data by rotating the phase of the saturation frequency offset complex image data for each of the voxels using the water phase angle such that the complex water signal is aligned with a real axis for each voxel
210 perform a B0 correction by calculating shifted complex image data using the rotated complex image data for each of the set of saturation frequency offsets and for each of the voxels using the B0 map
212 calculate a frequency dependent phase angle descriptive of the phase angle between the complex water signal and the complex fat signal for each of the set of saturation frequency offsets using a fat signal model comprising at least two fat species
214 calculate a residual fat component correction factor by projecting the complex fat signal onto the real axis for each of the set of saturation frequency offsets and for each of the voxels using the frequency dependent phase angle
216 calculate corrected water Z-spectrum image data by subtracting the residual fat component correction factor for each of the set of saturation frequency offsets and for each of the voxels from the real component of the shifted complex image data.

300 medical imaging system
302 magnetic resonance imaging system
304 magnet
306 bore of magnet
308 imaging zone
309 region of interest
310 magnetic field gradient coils
312 magnetic field gradient coil power supply
314 radio frequency coil
316 transceiver
318 subject
320 subject support
330 pulse sequence commands.
332 fat signal model calibration pulse sequence commands
334 calibration magnetic resonance data
400 control the magnetic resonance imaging system with the pulse sequence commands to acquire the magnetic resonance imaging data
600 plot illustrating fat signal model
602 further plot illustrating fat signal model
604 calculated fat signal
700 calculated fat signal vs saturation frequency offset
702 frequency dependent phase angle vs saturation frequency offset
704 sum of signal from all fat species
800 water signal
802 fat signal
804 magnitude
806 real axis
900 projection of magnitude onto real axis
902 real component of shifted complex image data
904 imaginary component of shifted complex image data
1000 symmetric model function
1002 region relevant for APTw imaging
1006 $MTR_{asym,FC}$
1008 $MTR_{asym}(M)$

The invention claimed is:

1. A medical imaging system, comprising:
a memory configured to store machine executable instructions;
a processor configured to control the medical imaging system, wherein execution of the machine executable instructions causes the processor to:
receive magnetic resonance imaging data, wherein the magnetic resonance imaging data comprises a Z-spectrum acquisition for a set of saturation frequency offsets and at least one reference saturation frequency offset, wherein the Z-spectrum acquisition is according to a CEST magnetic resonance imaging protocol, wherein the Z-spectrum acquisition for the at least one reference saturation frequency offset comprises data for multiple echo shifts or echo times, wherein the Z-spectrum acquisition for each of the set of saturation frequency offsets and the at least one reference saturation frequency offset is descriptive of complex image data comprising a complex water signal and a complex fat signal;
reconstruct saturation frequency offset complex image data for each of the set of saturation frequency offsets from the Z-spectrum acquisition, wherein the saturation frequency offset complex image data comprises voxels;
reconstruct a B0 map, a water image, and a fat image using the data for multiple echo shifts or echo times according to a Dixon-type magnetic resonance imaging protocol;
calculate a water phase angle using the water image and/or the fat image;
calculate rotated complex image data by rotating a phase of the saturation frequency offset complex image data for each of the voxels using the water phase angle such that the complex water signal is aligned with a real axis for each voxel;
perform a B0 correction by calculating shifted complex image data using the rotated complex image data for each of the set of saturation frequency offsets and for each of the voxels using the B0 map;
calculate a frequency dependent phase angle descriptive of a phase angle between the complex water signal and the complex fat signal for each of the set of saturation frequency offsets using a fat signal model comprising at least two fat species;
calculate a residual fat component correction factor by projecting the complex fat signal onto the real axis for each of the set of saturation frequency offsets and for each of the voxels using the frequency dependent phase angle; and
calculate corrected water Z-spectrum image data by subtracting the residual fat component correction factor for each of the set of saturation frequency offsets and for each of the voxels from a real component of the shifted complex image data;
wherein the medical imaging system further comprises a magnetic resonance imaging system configured for acquiring the magnetic resonance imaging data from a subject within an imaging zone, wherein the memory further stores pulse sequence commands, wherein the pulse sequence commands are configured to acquire the magnetic resonance data according to the CEST magnetic resonance imaging protocol, wherein execution of the machine executable instructions cause the processor to control the magnetic resonance imaging system with the pulse sequence commands to acquire the magnetic resonance imaging data.

2. The medical imaging system of claim 1, wherein the pulse sequence commands are configured to acquire the Z-spectrum acquisition for the set of saturation frequency offsets and the at least one reference saturation frequency offset with the complex water signal and the complex fat signal using any one of: a same echo shift or a same echo time; wherein the pulse sequence commands are configured to acquire the Z-spectrum acquisition for the at least one reference saturation frequency offset using at least one further echo shift or at least one further echo time.

3. The medical imaging system of claim 1, wherein the pulse sequence commands are configured to acquire the magnetic resonance data without fat suppression pulse sequence commands.

4. The medical imaging system of claim 1, wherein the pulse sequence commands are configured for using a specific echo shift or specific echo time such that the phase between the complex water signal and the complex fat signal is unequal to 0 degrees and unequal to 180 degrees when the set of saturation frequency offsets and the at least one reference saturation frequency offset use the same echo shift or the same echo time.

5. The medical imaging system of claim 1, wherein the memory further comprises fat calibration pulse sequence commands, wherein the fat calibration pulse sequence commands are configured for measuring a line width and/or one or more relaxation rates of the two or more fat species, wherein execution of the machine executable instructions further cause the processor to:
  acquire fat calibration magnetic resonance data by controlling the magnetic resonance imaging system with the fat calibration pulse sequence commands; and
  calibrate the fat signal model for the set of saturation frequency offsets using the fat calibration magnetic resonance data.

6. The medical imaging system of claim 1, wherein the phase between the complex water signal and the complex fat signal is within any one of the following ranges when the set of saturation frequency offsets and the at least one reference saturation frequency offset use the same echo shift or the same echo time:
  between 5 degrees and 175 degrees, and
  between 185 degrees and 355 degrees.

7. The medical imaging system of claim 1, wherein the Dixon magnetic resonance imaging protocol is a multi-point Dixon magnetic resonance imaging protocol configured for using at least two different echo shifts or two different echo times for reconstruction of the B0 map and a water image and/or a fat image.

8. The medical imaging system of claim 1, wherein the at least one reference saturation frequency offset is S0, and wherein S0 is any one of the following: a detuned frequency offset, less than −1000 ppm, and −1560 ppm, or wherein no saturation is applied.

9. The medical imaging system of claim 1, wherein execution of the machine executable instructions further causes the processor to calculate a fat corrected CEST magnetic resonance image using a corrected water Z-spectrum image data for each of the set of reference saturation frequency offsets.

10. The medical imaging system of claim 1, wherein execution of the machine executable instructions further causes the processor to calculate a fat corrected CEST magnetic resonance image using a corrected water Z-spectrum image data for each of the set of reference saturation frequency offsets by calculating a magnetization transfer asymmetry.

11. The medical imaging system of claim 1, wherein execution of the machine executable instructions further causes the processor to calculate a fat corrected CEST magnetic resonance image by:
  fitting a symmetric model function to a corrected water Z-spectrum image data for each of the set of reference saturation frequency offsets;
  calculating CEST MRI data by using a difference between the real component of the corrected water Z-spectrum image data and the symmetric model function at respective saturation frequency offsets;
  normalizing the CEST MRI data to S0; and
  calculating a CEST MR image using the normalized CEST MRI data.

12. The medical imaging system of claim 1, wherein the CEST magnetic resonance imaging protocol is an Amide Proton Transfer weighted magnetic resonance imaging protocol.

13. A method of operating a medical imaging system, wherein the method comprises:
  receiving magnetic resonance imaging data, wherein the magnetic resonance imaging data comprises a Z-spectrum acquisition for a set of saturation frequency offsets and at least one reference saturation frequency offset, wherein the Z-spectrum acquisition is according to a CEST magnetic resonance imaging protocol, wherein the Z-spectrum acquisition for the at least one reference saturation frequency offset comprises data for multiple echo shifts or multiple echo times, wherein the Z-spectrum acquisition for each of the set of frequency offsets and the at least one reference saturation frequency offset is descriptive of complex image data comprising a complex water signal and a complex fat signal;
  reconstructing saturation frequency offset complex image data for each of the set of saturation frequency offsets from the Z-spectrum acquisition, wherein the saturation frequency offset complex image data comprises voxels;
  reconstructing a B0 map, a water image, and a fat image using the data for multiple echo shifts or multiple echo times according to a Dixon-type magnetic resonance imaging protocol;
  calculating a water phase angle using the water image and/or the fat image;
  calculating rotated complex image data by rotating a phase of the saturation frequency complex offset image data for each of the voxels using the water phase angle such that the complex water signal is aligned with a real axis for each voxel;
  performing a B0 correction by calculating shifted complex image data using the rotated complex image data for each of the set of saturation frequency offsets and for each of the voxels using the B0 map;
  calculating a frequency dependent phase angle descriptive of a phase angle between the complex water signal and the complex fat signal for each of the set of saturation frequency offsets using a fat signal model comprising at least two fat species;
  calculating a residual fat component correction factor by projecting the complex fat signal onto the real axis for each of the set of saturation frequency offsets and for each of the voxels using the frequency dependent phase angle; and
  calculating corrected water Z-spectrum image data by subtracting the residual fat component correction factor for each of the set of saturation frequency offsets and for each of the voxels from a real component of a shifted complex image data;
  wherein the medical imaging system further comprises a magnetic resonance imaging system configured for acquiring the magnetic resonance imaging data from a subject within an imaging zone, wherein a memory further stores pulse sequence commands, wherein the pulse sequence commands are configured to acquire the magnetic resonance data according to the CEST magnetic resonance imaging protocol, wherein execution of machine executable instructions cause a processor to control the magnetic resonance imaging system with the pulse sequence commands to acquire the magnetic resonance imaging data.

14. A computer program product comprising machine executable instructions for execution by a processor controlling a medical imaging system, wherein execution of the machine executable instructions cause the processor to:
  receive magnetic resonance imaging data, wherein the magnetic resonance imaging data comprises a Z-spectrum acquisition) for a set of saturation frequency offsets and at least one reference saturation frequency offset, wherein the Z-spectrum acquisition is according to a CEST magnetic resonance imaging protocol, wherein the Z-spectrum acquisition for the at least one reference saturation frequency offset comprises data for multiple echo shifts or echo times, wherein the Z-spectrum acquisition for each of the set of frequency offsets and the at least one reference saturation frequency offset is descriptive of complex image data comprising a complex water signal and a complex fat signal;

reconstruct saturation frequency offset complex image data for each of the set of saturation frequency offsets from the Z-spectrum acquisition, wherein the saturation frequency offset complex image data comprises voxels;

reconstruct a B0 map, a water image, and a fat image using the data for multiple echo shifts or echo times according to a Dixon-type magnetic resonance imaging protocol;

calculate a water phase angle (138) using the water image and/or the fat image;

calculate rotated complex image data by rotating a phase of the saturation frequency complex offset image data for each of the voxels using the water phase angle such that the complex water signal is aligned with a real axis for each voxel;

perform a B0 correction by calculating shifted complex image data using the rotated complex image data for each of the set of saturation frequency offsets and for each of the voxels using the B0 map;

calculate a frequency dependent phase angle descriptive of a phase angle between the complex water and the complex fat signal for each of the set of saturation frequency offsets using a fat signal model comprising at least two fat species;

calculate a residual fat component correction factor by projecting the complex fat signal onto the real axis for each of the set of saturation frequency offsets and for each of the voxels using the saturation frequency offset dependent phase angle; and calculate corrected water Z-spectrum image data by subtracting the residual fat component correction factor for each of the set of saturation frequency offsets and for each of the voxels from a real component of the shifted complex image data;

wherein the medical imaging system further comprises a magnetic resonance imaging system configured for acquiring the magnetic resonance imaging data from a subject within an imaging zone, wherein a memory further stores pulse sequence commands, wherein the pulse sequence commands are configured to acquire the magnetic resonance data according to the CEST magnetic resonance imaging protocol, wherein execution of the machine executable instructions cause the processor to control the magnetic resonance imaging system with the pulse sequence commands to acquire the magnetic resonance imaging data.

\* \* \* \* \*